(12) United States Patent
Stephanopoulos et al.

(10) Patent No.: US 9,284,570 B2
(45) Date of Patent: *Mar. 15, 2016

(54) MICROBIAL PRODUCTION OF NATURAL SWEETENERS, DITERPENOID STEVIOL GLYCOSIDES

(75) Inventors: Gregory Stephanopoulos, Winchester, MA (US); Parayil K. Ajikumar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 887 days.

This patent is subject to a terminal disclaimer.

(21) Appl. No.: 13/306,633

(22) Filed: Nov. 29, 2011

(65) Prior Publication Data

US 2012/0164678 A1  Jun. 28, 2012

Related U.S. Application Data

(63) Continuation-in-part of application No. 13/249,388, filed on Sep. 30, 2011, now Pat. No. 8,927,241.

(60) Provisional application No. 61/418,357, filed on Nov. 30, 2010.

(51) Int. Cl.

| C12P 15/00 | (2006.01) |
|---|---|
| C12N 9/90 | (2006.01) |
| C12N 9/88 | (2006.01) |
| C12N 9/10 | (2006.01) |
| C12N 9/02 | (2006.01) |
| C12N 9/12 | (2006.01) |
| C12N 15/00 | (2006.01) |
| C12N 1/20 | (2006.01) |
| C07H 21/04 | (2006.01) |
| C12N 15/82 | (2006.01) |
| C12N 15/70 | (2006.01) |
| A01H 5/00 | (2006.01) |
| A01H 13/00 | (2006.01) |
| A23L 1/236 | (2006.01) |
| A23L 2/60 | (2006.01) |
| C12P 7/42 | (2006.01) |
| C12P 17/02 | (2006.01) |

(52) U.S. Cl.
CPC .............. *C12N 15/8243* (2013.01); *A01H 5/00* (2013.01); *A01H 13/00* (2013.01); *A23L 1/2366* (2013.01); *A23L 2/60* (2013.01); *C12N 9/0042* (2013.01); *C12N 9/0073* (2013.01); *C12N 9/0085* (2013.01); *C12N 9/1085* (2013.01); *C12N 9/1288* (2013.01); *C12N 9/88* (2013.01); *C12N 9/90* (2013.01); *C12N 15/70* (2013.01); *C12P 7/42* (2013.01); *C12P 15/00* (2013.01); *C12P 17/02* (2013.01); *C12Y 106/02004* (2013.01); *C12Y 114/13* (2013.01); *C12Y 114/13076* (2013.01); *C12Y 114/13078* (2013.01); *C12Y 114/99009* (2013.01); *C12Y 205/01029* (2013.01); *C12Y 402/03019* (2013.01); *C12Y 505/01012* (2013.01); *C12Y 505/01013* (2013.01); *Y02P 20/52* (2015.11)

(58) Field of Classification Search
CPC .......... C12N 9/90; C12N 9/88; C12N 9/1085; C12N 9/0073; C12N 9/1288; C12N 15/70; C12P 15/00
See application file for complete search history.

(56) References Cited

U.S. PATENT DOCUMENTS

| 8,512,988 | B2 | 8/2013 | Ajikumar et al. |
|---|---|---|---|
| 8,927,241 | B2 | 1/2015 | Ajikumar et al. |
| 2004/0072323 | A1 | 4/2004 | Matsuda et al. |
| 2007/0026484 | A1 | 2/2007 | Kinney et al. |
| 2008/0274523 | A1 | 11/2008 | Renninger et al. |
| 2010/0297722 | A1 | 11/2010 | Anterola et al. |
| 2012/0107893 | A1 | 5/2012 | Ajikumar et al. |
| 2013/0171328 | A1* | 7/2013 | Kishore et al. ................ 426/658 |
| 2014/0024089 | A1 | 1/2014 | Ajikumar et al. |

FOREIGN PATENT DOCUMENTS

| WO | WO 97/38571 | A1 | 10/1997 |
|---|---|---|---|
| WO | WO 2008/128159 | * | 10/2008 |

OTHER PUBLICATIONS

Richman et al. Diterpene synthesis in Stevia rebaudiana: recruitment and up-regulation of key enzymes from the gibberellin biosynthetic pathway. Plant J. Aug. 1999;19(4):411-21.*
Liao et al. Cloning and functional expression of a cDNA encoding geranylgeranyl diphosphate synthase from Taxus canadensis and assessment of the role of this prenyltransferase in cells induced for taxol production. Arch Biochem Biophys. Dec. 1, 1998;360(1):62-74.*
Stewart et al Biotechnology and Genetic Engineering Reviews, 14:67-143, 1997.*
Genbank Submission; NIH/NCBI, Accession No. AAN01134; Burke et al.; Aug. 29, 2002.
Genbank Submission; NIH/NCBI, Accession No. U87908; Bohlmann et al.; Sep. 24, 2007.
Genbank Submission; NIH/NCBI, Accession No. AY195608; Dudareva et al.; May 3, 2003.
Genbank Submission; NIH/NCBI, Accession No. AF271259; Hosoi et al.; Feb. 3, 2005.

(Continued)

*Primary Examiner* — Yong Pak
(74) *Attorney, Agent, or Firm* — Wolf, Greenfield & Sacks, P.C.

(57) ABSTRACT

The invention relates to recombinant expression of a steviol or steviol glycosides biosynthetic pathway enzymes in cells and the production of steviol or steviol glycosides.

15 Claims, 4 Drawing Sheets

(56) References Cited

OTHER PUBLICATIONS

Ajikumar et al., Isoprenoid pathway optimization for Taxol precursor overproduction in *Escherichia coli*. Science. Oct. 1, 2010;330(6000):70-4.

Ajikumar et al., Terpenoids: opportunities for biosynthesis of natural product drugs using engineered microorganisms. Mol Pharm. Mar.-Apr. 2008;5(2):167-90. Epub Mar. 21, 2008.

Alper et al., Construction of lycopene-overproducing *E. coli* strains by combining systematic and combinatorial gene knockout targets. Nat Biotechnol. May 2005;23(5):612-6. Epub Apr. 10, 2005.

Behr et al., Myrcene as a natural base chemical in sustainable chemistry: a critical review. ChemSusChem. 2009;2(12):1072-95. doi: 10.1002/cssc.200900186.

Bohlmann et al., Monoterpene synthases from grand fir (Abies grandis). cDNA isolation, characterization, and functional expression of myrcene synthase, (31 )-(4S)-limonene synthase, and (–)-(1S,5S)-pinene synthase. J Biol Chem. Aug. 29, 1997;272(35):21784-92.

Brandle et al., Steviol glycoside biosynthesis. Phytochemistry. Jul. 2007;68(14):1855-63. Epub Mar. 29, 2007.

Brosius et al., Spacing of the -10 and -35 regions in the tac promoter. Effect on its in vivo activity. J Biol Chem. Mar. 25, 1985;260(6):3539-41.

Broun et al., Catalytic plasticity of fatty acid modification enzymes underlying chemical diversity of plant lipids. Science. Nov. 13, 1998;282(5392):1315-7.

Brunner et al., Promoter recognition and promoter strength in the *Escherichia coli* system. EMBO J. Oct. 1987;6(10):3139-44.

Chang et al., Engineering *Escherichia coli* for production of functionalized terpenoids using plant P450s. Nat Chem Biol. May 2007;3(5):274-7. Epub Apr. 15, 2007.

Chang et al., Gene expression profiling of *Escherichia coli* growth transitions: an expanded stringent response model. Mol Microbiol. Jul. 2002;45(2):289-306.

Chang et al., Production of isoprenoid pharmaceuticals by engineered microbes. Nat Chem Biol. Dec. 2006;2(12):674-81.

Chau et al., Taxol biosynthesis: Molecular cloning and characterization of a cytochrome P450 taxoid 7 beta-hydroxylase. Chem Biol. May 2004;11(5):663-72.

Chica et al., Semi-rational approaches to engineering enzyme activity: combining the benefits of directed evolution and rational design. Curr Opin Biotechnol. Aug. 2005;16(4):378-84.59rt.

Croteau et al., Taxol biosynthesis and molecular genetics. Phytochem Rev. Feb. 2006;5(1):75-97.

Das et al., An update on microbial carotenoid production: application of recent metabolic engineering tools. Appl Microbiol Biotechnol. Dec. 2007;77(3):505-12. Epub Oct. 3, 2007.

Datsenko et al., One-step inactivation of chromosomal genes in *Escherichia coli* K-12 using PCR products. Proc Natl Acad Sci U S A. Jun. 6, 2000;97(12):6640-5.

Dejong et al., Genetic engineering of taxol biosynthetic genes in *Saccharomyces cerevisiae*. Biotechnol Bioeng. Feb. 5, 2006;93(2):212-24.

Devos et al., Practical limits of function prediction. Proteins. Oct. 1, 2000;41(1):98-107.

Engels et al., Metabolic engineering of taxadiene biosynthesis in yeast as a first step towards Taxol (Paclitaxel) production. Metab Eng. May-Jul. 2008;10(3-4):201-6. doi: 10.1016/j.ymben.2008.03.001. Epub Mar. 26, 2008.

Farmer et al., Improving lycopene production in *Escherichia coli* by engineering metabolic control. Nat Biotechnol. May 2000;18(5):533-7.

Farmer et al., Precursor balancing for metabolic engineering of lycopene production in *Escherichia coli*. Biotechnol Prog. Jan.-Feb. 2001;17(1):57-61.

Frense, Taxanes: perspectives for biotechnological production. Appl Microbiol Biotechnol. Jan. 2007;73(6):1233-40. Epub Nov. 24, 2006.

Hefner et al., Cloning and functional expression of a cDNA encoding geranylgeranyl diphosphate synthase from Taxus canadensis and assessment of the role of this prenyltransferase in cells induced for taxol production. Arch Biochem Biophys. Dec. 1, 1998;360(1):62-74.

Heinig et al., Taxol: A complex diterpenoid natural product with an evolutionarily obscure origin. African J Biotechnol. 2009;8:1370-85.

Hoffmann et al., Metabolic adaptation of *Escherichia coli* during temperature-induced recombinant protein production: 1. Readjustment of metabolic enzyme synthesis. Biotechnol Bioeng. Nov. 5, 2002;80(3):313-9.

Hoffmann et al., Stress induced by recombinant protein production in *Escherichia coli*. Adv Biochem Eng Biotechnol. 2004;89:73-92.

Holton et al., First total synthesis of taxol. 2. Completion of the C and D rings. J. Am. Chem. Soc. Feb. 1994;116 (4):1599-1600.

Huang et al., Engineering *Escherichia coli* for the synthesis of taxadiene, a key intermediate in the biosynthesis of taxol. Bioorg Med Chem. Sep. 2001;9(9):2237-42.

Hughes et al., Metabolic engineering of the indole pathway in Catharanthus roseus hairy roots and increased accumulation of tryptamine and serpentine. Metab Eng. Oct. 2004;6(4):268-76.

Humphrey et al., Spatial organisation of four enzymes from Stevia rebaudiana that are involved in steviol glycoside synthesis. Plant Mol Biol. May 2006;61(1-2):47-62.

Jennewein et al., Coexpression in yeast of Taxus cytochrome P450 reductase with cytochrome P450 oxygenases involved in Taxol biosynthesis. Biotechnol Bioeng. Mar. 5, 2005;89(5):588-98.

Jennewein et al., Cytochrome p450 taxadiene 5alpha-hydroxylase, a mechanistically unusual monooxygenase catalyzing the first oxygenation step of taxol biosynthesis. Chem Biol. Mar. 2004;11(3):379-87.

Jennewein et al., Random sequencing of an induced Taxus cell cDNA library for identification of clones involved in Taxol biosynthesis. Proc Natl Acad Sci U S A. Jun. 15, 2004;101(24):9149-54. Epub Jun. 3, 2004.

Jennewein et al., Taxol: biosynthesis, molecular genetics, and biotechnological applications. Appl Microbiol Biotechnol. Oct. 2001;57(1-2):13-9.

Tin et al., Multi-dimensional gene target search for improving lycopene biosynthesis in *Escherichia coli*. Metab Eng. Jul. 2007;9(4):337-47. Epub Apr. 12, 2007.

Jones et al., Low-copy plasmids can perform as well as or better than high-copy plasmids for metabolic engineering of bacteria. Metab Eng. Oct. 2000;2(4):328-38.

Kaspera et al., Cytochrome P450 oxygenases of Taxol biosynthesis. Phytochem Rev. Jun. 2006; 5(2-3): 433-444. doi: 10.1007/s11101-006-9006-4.

Khosla et al., Metabolic engineering for drug discovery and development. Nat Rev Drug Discov. Dec. 2003;2(12):1019-25.

Kim et al., Metabolic engineering of the nonmevalonate isopentenyl diphosphate synthesis pathway in *Escherichia coli* enhances lycopene production. Biotechnol Bioeng. Feb. 20, 2001;72(4):408-15.

Kimchi-Sarfaty et al., A "silent" polymorphism in the MDR1 gene changes substrate specificity. Science. Jan. 26, 2007;315(5811):525-8. Epub Dec. 21, 2006. Erratum in: Science. Oct. 7, 2011;334(6052):39. Science. Nov. 30, 2007;318(5855):1382-3.

Kingston, The shape of things to come: structural and synthetic studies of taxol and related compounds. Phytochemistry. Jul. 2007;68(14):1844-54. Epub Dec. 20, 2006.

Kirby et al., Biosynthesis of plant isoprenoids: perspectives for microbial engineering. Annu Rev Plant Biol. 2009;60:335-55.

Kisselev, Polypeptide release factors in prokaryotes and eukaryotes: same function, different structure. Structure. Jan. 2002;10(1):8-9.

Klein-Marcuschamer et al., Engineering microbial cell factories for biosynthesis of isoprenoid molecules: beyond lycopene. Trends Biotechnol. Sep. 2007;25(9):417-24. Epub Aug. 2, 2007.

Kodumal et al., Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.

Leonard et al., Combining metabolic and protein engineering of a terpenoid biosynthetic pathway for overproduction and selectivity control. Proc Natl Acad Sci U S A. Aug. 3, 2010;107(31):13654-9. Epub Jul. 19, 2010.

(56) References Cited

OTHER PUBLICATIONS

Leonard et al., Engineering of artificial plant cytochrome P450 enzymes for synthesis of isoflavones by *Escherichia coli*. Appl Environ Microbiol. Nov. 2007;73(22):7246-51. Epub Sep. 28, 2007.

Liao, Molecular biology of the biosynthetic pathways of taxol precursors and metabolic engineering of anti-tumor terpenoid indole alkaloids. China doctor dissertation. Jan. 31, 2006. 1-157.

Martin et al., Engineering a mevalonate pathway in *Escherichia coli* for production of terpenoids. Nat Biotechnol. Jul. 2003;21(7):796-802. Epub Jun. 1, 2003.

Morrone et al., Increasing diterpene yield with a modular metabolic engineering system in *E. coli*: comparison of MEV and MEP isoprenoid precursor pathway engineering. Appl Microbiol Biotechnol. Feb. 2010;85(6):1893-906. doi: 10.1007/s00253-009-2219-x. Epub Sep. 24, 2009.

Nackley et al., Human catechol-O-methyltransferase haplotypes modulate protein expression by altering mRNA secondary structure. Science. Dec. 22, 2006;314(5807):1930-3.

Nelson, Cytochrome P450 and the individuality of species. Arch Biochem Biophys. Sep. 1, 1999;369(1):1-10.

Nicolaou, et al. Total synthesis of taxol. Nature. Feb. 17, 1994;367(6464):630-4.

Nishizaki et al., Metabolic Engineering of Carotenoid Biosynthesis in *Escherichia coli* by Ordered Gene Assembly in Bacillus subtilis. Appl Environ Microbiol. Feb. 2007; 73(4): 1355-1361.

Roberts, Production and engineering of terpenoids in plant cell culture. Nat Chem Biol. Jul. 2007;3(7):387-95.

Rontein et al., CYP725A4 from yew catalyzes complex structural rearrangement of taxa-4(5),11(12)-diene into the cyclic ether 5(12)-oxa-3(11)-cyclotaxane. J Biol Chem. Mar. 7, 2008;283(10):6067-75. doi: 10.1074/jbc.M708950200. Epub Dec. 31, 2007.

Rost et al., The PredictProtein server. Nucleic Acids Res. Jul. 1, 2004;32(Web Server issue):W321-6.

Sandmann, Combinatorial biosynthesis of carotenoids in a heterologous host: a powerful approach for the biosynthesis of novel structures. Chembiochem. Jul. 2, 2002;3(7):629-35.

Sauna et al., Silent polymorphisms speak: how they affect pharmacogenomics and the treatment of cancer. Cancer Res. Oct. 15, 2007;67(20):9609-12.

Schuler et al., Functional genomics of P450s. Annu Rev Plant Biol. 2003;54:629-67.

Seffernick et al., Melamine deaminase and atrazine chlorohydrolase: 98 percent identical but functionally different. J Bacteriol. Apr. 2001;183(8):2405-10.

Sen et al., Developments in directed evolution for improving enzyme functions. Appl Biochem Biotechnol. Dec. 2007;143(3):212-23.

Shalel-Levanon et al., Effect of ArcA and FNR on the expression of genes related to the oxygen regulation and the glycolysis pathway in *Escherichia coli* under microaerobic growth conditions. Biotechnol Bioeng. Oct. 20, 2005;92(2):147-59.

Shigemori et al., Biological activity and chemistry of taxoids from the Japanese yew, Taxus cuspidata J Nat Prod. Feb. 2004;67(2):245-56.

Sørensen et al., Advanced genetic strategies for recombinant protein expression in *Escherichia coli*. J Biotechnol. Jan. 26, 2005;115(2):113-28.

Trapp et al., Genomic organization of plant terpene synthases and molecular evolutionary implications. Genetics. Jun. 2001;158(2):811 32.

Tyo et al., Expanding the metabolic engineering toolbox: more options to engineer cells. Trends Biotechnol. Mar. 2007;25(3):132-7. Epub Jan. 24, 2007.

Tyo et al., Stabilized gene duplication enables long-term selection-free heterologous pathway expression. Nat Biotechnol. Aug. 2009;27(8):760-5. doi: 10.1038/nbt.1555. Epub Jul. 26, 2009.

Walji et al., Strategies to Bypass the Taxol Problem: Enantioselective Cascade Catalysis, A New Approach for the Efficient Construction of Molecular Complexity. Synlett. 2007;10:1477-1489.

Walker et al., Taxol biosynthetic genes. Phytochemistry. Sep. 2001;58(1):1-7.

Wang et al., Programming cells by multiplex genome engineering and accelerated evolution. Nature. Aug. 2009;460:894-898.

Wani et al., Plant antitumor agents. VI. The isolation and structure of taxol, a novel antileukemic and antitumor agent from Taxus brevifolia. J Am Chem Soc. May 5, 1971;93(9):2325-7.

Whisstock et al., Prediction of protein function from protein sequence and structure. Q Rev Biophys. Aug. 2003;36(3):307-40.

Whitmer et al., Influence of Precursor Availability on Alkaloid Accumulation by Transgenic Cell Line of Catharanthus roseus. Plant Physiol. Feb. 1, 1998;116(2):853-7.

Wildung et al., A cDNA clone for taxadiene synthase, the diterpene cyclase that catalyzes the committed step of taxol biosynthesis. J Biol Chem. Apr. 19, 1996;271(16):9201-4.

Williams et al., Heterologous expression and characterization of a "Pseudomature" form of taxadiene synthase involved in paclitaxel (Taxol) biosynthesis and evaluation of a potential intermediate and inhibitors of the multistep diterpene cyclization reaction. Arch Biochem Biophys. Jul. 1, 2000;379(1):137-46.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Xu et al., Strain improvement and optimization of the media of taxol-producing fungus Fusarium maire. Biochem Engineer J. Aug. 2006;31(1):67-73.

Yang et al., Metabolic engineering of *Escherichia coli* for the biosynthesis of alpha-pinene. Biotechnol Biofuels. Apr. 30, 2013;6(1):60. doi: 10.1186/1754-6834-6-60.

Yuan et al., Chromosomal promoter replacement of the isoprenoid pathway for enhancing carotenoid production in *E. coli*. Metab Eng. Jan. 2006;8(1):79-90. Epub Oct. 28, 2005.

Genbank Submission; NCBI, Accession No. AF081514; Hefner et al.; May 1, 2001.

Genbank Submission; NCBI, Accession No. ABD92926; Kumar et al.; Oct. 10, 2007.

Genbank Submission; NCBI, Accession No. AAB87091; Richman et al.; Mar. 22, 2000.

Genbank Submission; NCBI, Accession No. AF097311_1; Richman et al.; Mar. 22, 2000.

Genbank Submission; NCBI, Accession No. ABA42921; Humphrey et al.; Jun. 21, 2006.

Genbank Submission; NCBI, Accession No. ACD93722; Reeja et al.; Jun. 10, 2008.

Genbank Submission; NCBI, Accession No. AY571340; Jennewein et al.; Jan. 20, 2010.

Genbank Submission; NCBI, Accession No. ABB88839; Kumar et al.; May 28, 2008.

Genbank Submission; NCBI, Accession No. AAM53963; Ma et al.; Jun. 17, 2002.

Genbank Submission; NCBI, Accession No. AAR06921; Richman et al.; Dec. 28, 2004.

Genbank Submission; NCBI, Accession No. AAR06920; Richman et al.; Dec. 28, 2004.

Genbank Submission; NCBI, Accession No. AAR06917; Richman et al.; Dec. 28, 2004.

Genbank Submission; NCBI, Accession No. AAN40684; Ma et al.; Oct. 14, 2002.

Genbank Submission; NCBI, Accession No. ACE87855; Joseph et al.; Jun. 24, 2008.

Balderas-Hernández et al., Metabolic engineering for improving anthranilate synthesis from glucose in *Escherichia coli*. Microb Cell Fact. Apr. 2, 2009;8:19. doi: 10.1186/1475-2859-8-19.

Burke et al., Geranyl diphosphate synthase from Abies grandis: cDNA isolation, functional expression, and characterization. Arch Biochem Biophys. Sep. 1, 2002;405(1):130-6.

Carakostas et al., Overview: the history, technical function and safety of rebaudioside A, a naturally occurring steviol glycoside, for use in food and beverages. Food Chem Toxicol. Jul. 2008;46 Suppl 7:S1-S10. doi: 10.1016/j.fct.2008.05.003. Epub May 16, 2008.

(56) References Cited

OTHER PUBLICATIONS

Dagnino et al., Terpenoid indole alkaloid biosynthesis and enzyme-activities in two cell-lines of Tabernaemontana divaricata. Phytochemistry. 1995;39(2):341-349.

Geuns, Steviol glycosides as food additive. Eustas. Sep. 26, 2007. 1-20.

Geuns, Stevioside. Phytochemistry. Nov. 2003;64(5):913-21.

Gibson et al., Creation of a bacterial cell controlled by a chemically synthesized genome. Science. Jul. 2, 2010;329(5987):52-6. doi: 10.1126/science.1190719. Epub May 20, 2010.

Mishra et al., Stevia Rebaudiana—A Magical Sweetener. Global J Biotechnology Biochemistry. 2010;5(1):62-74.

Moreno et al., Effects of elicitation on different metabolic pathways in Catharanthus roseus (L.)G.Don cell suspension cultures. Enzyme Micro Tech. 1996;18:99-107.

Richman et al., Functional genomics uncovers three glucosyltransferases involved in the synthesis of the major sweet glucosides of Stevia rebaudiana. Plant J. Jan. 2005;41(1):56-67.

Sharma et al., Chemistry and in vivo profile of ent-kaurene glycosides of Stevia rebaudiana Bertoni—an overview. Natural Product Radiance. 2009;8(2):181-189.

Singh et al., Stevia: The herbal sugar of 21st century. Sugar Tech. Mar. 2005;7(1):17-24.

Ulbricht et al., An evidence-based systematic review of stevia by the Natural Standard Research Collaboration. Cardiovasc Hematol Agents Med Chem. Apr. 2010;8(2):113-27.

Veau et al., Cloning and expression of cDNAs encoding two enzymes of the MEP pathway in Catharanthus roseus. Biochim Biophys Acta. Dec. 15, 2000;1517(1):159-63.

Verpoorte et al., Plant cell biotechnology for the production of secondary metabolites. Pure & Appl. Chem. 1994:66:2307-2310.

Stephanopoulos, Bioreaction network analysis: A central component of microbe and metabolic engineering. Annual AIChE Meeting—2009. Session honoring Professor James Wei. Nashville, TN. Nov. 9, 2009.

Stephanopoulos, Engineering microbes for biofuel production. TMFB Tailor Made Fuels from Biomass, $2^{nd}$ International Workshop. RW Technical University. Jun. 24-25, 2009.

Verpoorte et al., Biotechnology for the production of plant secondary metabolites. Phyto Rev. 2002;1(1):13-25.

\* cited by examiner

SEQUENCE LISTING

```
<160> NUMBER OF SEQ ID NOS: 39

<210> SEQ ID NO 1
<211> LENGTH: 296
<212> TYPE: PRT
<213> ORGANISM: Taxus canadensis

<400> SEQUENCE: 1

Met Phe Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
            20                  25                  30

Glu Ser Met Arg Tyr Ser Leu Leu Ala Gly Gly Lys Arg Val Arg Pro
        35                  40                  45

Ala Leu Cys Ile Ala Ala Cys Glu Leu Val Gly Gly Ser Gln Asp Leu
    50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95
```

```
Lys Pro Thr Asn His Lys Val Phe Gly Glu Asp Thr Ala Val Leu Ala
            100                 105                 110

Gly Asp Ala Leu Leu Ser Phe Ala Phe Glu His Ile Ala Val Ala Thr
        115                 120                 125

Ser Lys Thr Val Pro Ser Asp Arg Thr Leu Arg Val Ile Ser Glu Leu
    130                 135                 140

Gly Lys Thr Ile Gly Ser Gln Gly Leu Val Gly Gln Val Val Asp
145                 150                 155                 160

Ile Thr Ser Glu Gly Asp Ala Asn Val Asp Leu Lys Thr Leu Glu Trp
                165                 170                 175

Ile His Ile His Lys Thr Ala Val Leu Glu Cys Ser Val Val Ser
            180                 185                 190

Gly Gly Ile Leu Gly Gly Ala Thr Glu Asp Glu Ile Ala Arg Ile Arg
        195                 200                 205

Arg Tyr Ala Arg Cys Val Gly Leu Leu Phe Gln Val Val Asp Asp Ile
    210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu
                245                 250                 255

Lys Ala Lys Glu Phe Ala Ala Glu Leu Ala Thr Arg Ala Lys Glu Glu
            260                 265                 270

Leu Ser Ser Phe Asp Gln Ile Lys Ala Ala Pro Leu Leu Gly Leu Ala
        275                 280                 285

Asp Tyr Ile Ala Phe Arg Gln Asn
    290                 295

<210> SEQ ID NO 2
<211> LENGTH: 361
<212> TYPE: PRT
<213> ORGANISM: Stevia rebaudiana

<400> SEQUENCE: 2

Met Ala Leu Val Asn Pro Thr Ala Leu Phe Tyr Gly Thr Ser Ile Arg
1               5                   10                  15

Thr Arg Pro Thr Asn Leu Leu Asn Pro Thr Gln Lys Leu Arg Pro Val
            20                  25                  30

Ser Ser Ser Ser Leu Pro Ser Phe Ser Ser Val Ser Ala Ile Leu Thr
        35                  40                  45

Glu Lys His Gln Ser Asn Pro Ser Glu Asn Asn Leu Gln Thr His
    50                  55                  60

Leu Glu Thr Pro Phe Asn Phe Asp Ser Tyr Met Leu Glu Lys Val Asn
65                  70                  75                  80

Met Val Asn Glu Ala Leu Asp Ala Ser Val Pro Leu Lys Asp Pro Ile
            85                  90                  95

Lys Ile His Glu Ser Met Arg Tyr Ser Leu Leu Ala Gly Gly Lys Arg
        100                 105                 110

Ile Arg Pro Met Met Cys Ile Ala Ala Cys Glu Ile Val Gly Gly Asn
    115                 120                 125

Ile Leu Asn Ala Met Pro Ala Ala Cys Ala Val Glu Met Ile His Thr
130                 135                 140

Met Ser Leu Val His Asp Asp Leu Pro Cys Met Asp Asn Asp Asp Phe
145                 150                 155                 160

Arg Arg Gly Lys Pro Ile Ser His Lys Val Tyr Gly Glu Glu Met Ala
```

```
                165                 170                 175
Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Pro Leu Ile Ala Leu
            340                 345                 350

Ala Asn Tyr Asn Ala Tyr Arg Gln Asn
        355                 360

<210> SEQ ID NO 3
<211> LENGTH: 787
<212> TYPE: PRT
<213> ORGANISM: Stevia rebaudiana

<400> SEQUENCE: 3

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175
```

-continued

Pro Ser Lys Cys Glu Lys Gly Leu Asn Phe Leu Arg Glu Asn Ile Cys
            180                 185                 190

Lys Leu Glu Asp Glu Asn Ala Glu His Met Pro Ile Gly Phe Glu Val
            195                 200             205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350

Tyr Ile Asn Lys Tyr Trp Thr Lys Asn Gly Ile Cys Trp Ala Arg Asn
        355                 360                 365

Thr His Val Gln Asp Ile Asp Asp Thr Ala Met Gly Phe Arg Val Leu
    370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
            420                 425                 430

Glu Arg Ile Leu Glu Asp Ala Lys Lys Phe Ser Tyr Asn Tyr Leu Lys
        435                 440                 445

Glu Lys Gln Ser Thr Asn Glu Leu Leu Asp Lys Trp Ile Ile Ala Lys
    450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
            500                 505                 510

Ser Asn Asn Thr Tyr Leu Glu Met Ala Lys Leu Asp Tyr Asn Asn Tyr
        515                 520                 525

Val Ala Val Leu Gln Leu Glu Trp Tyr Thr Ile Gln Gln Trp Tyr Val
    530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ser Ile Phe Glu Pro Glu Arg Ser
                565                 570                 575

Lys Glu Arg Ile Ala Trp Ala Lys Thr Thr Ile Leu Val Asp Lys Ile
            580                 585                 590

Thr Ser Ile Phe Asp Ser Ser Gln Ser Ser Lys Glu Asp Ile Thr Ala

```
                    595                 600                 605
Phe Ile Asp Lys Phe Arg Asn Lys Ser Ser Lys Lys His Ser Ile
    610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
                660                 665                 670

Gly Val Asp Val Thr Ala Glu Leu Met Val Gln Met Ile Asn Met Thr
            675                 680                 685

Ala Gly Arg Trp Val Ser Lys Glu Leu Leu Thr His Pro Gln Tyr Gln
690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                725                 730                 735

Leu Val Gln Leu Val Phe Ser Asp Thr Pro Asp Asp Leu Asp Gln Asp
            740                 745                 750

Met Lys Gln Thr Phe Leu Thr Val Met Lys Thr Phe Tyr Tyr Lys Ala
        755                 760                 765

Trp Cys Asp Pro Asn Thr Ile Asn Asp His Ile Ser Lys Val Phe Glu
770                 775                 780

Ile Val Ile
785

<210> SEQ ID NO 4
<211> LENGTH: 784
<212> TYPE: PRT
<213> ORGANISM: Stevia rebaudiana

<400> SEQUENCE: 4

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175
```

-continued

```
Asp Ile Asn Leu Leu Ser Lys Gln Thr Asp Phe Ser Leu Met Leu His
            180                 185                 190
Lys Arg Glu Leu Glu Gln Lys Arg Cys His Ser Asn Glu Met Asp Gly
        195                 200                 205
Tyr Leu Ala Tyr Ile Ser Glu Gly Leu Gly Asn Leu Tyr Asp Trp Asn
        210                 215                 220
Met Val Lys Lys Tyr Gln Met Lys Asn Gly Ser Val Phe Asn Ser Pro
225                 230                 235                 240
Ser Ala Thr Ala Ala Phe Ile Asn His Gln Asn Pro Gly Cys Leu
            245                 250                 255
Asn Tyr Leu Asn Ser Leu Leu Asp Lys Phe Gly Asn Ala Val Pro Thr
        260                 265                 270
Val Tyr Pro His Asp Leu Phe Ile Arg Leu Ser Met Val Asp Thr Ile
        275                 280                 285
Glu Arg Leu Gly Ile Ser His His Phe Arg Val Glu Ile Lys Asn Val
        290                 295                 300
Leu Asp Glu Thr Tyr Arg Cys Trp Val Glu Arg Asp Glu Gln Ile Phe
305                 310                 315                 320
Met Asp Val Val Thr Cys Ala Leu Ala Phe Arg Leu Leu Arg Ile Asn
            325                 330                 335
Gly Tyr Glu Val Ser Pro Asp Pro Leu Ala Glu Ile Thr Asn Glu Leu
        340                 345                 350
Ala Leu Lys Asp Glu Tyr Ala Ala Leu Glu Thr Tyr His Ala Ser His
        355                 360                 365
Ile Leu Tyr Gln Glu Asp Leu Ser Ser Gly Lys Gln Ile Leu Lys Ser
        370                 375                 380
Ala Asp Phe Leu Lys Glu Ile Ile Ser Thr Asp Ser Asn Arg Leu Ser
385                 390                 395                 400
Lys Leu Ile His Lys Glu Val Glu Asn Ala Leu Lys Phe Pro Ile Asn
            405                 410                 415
Thr Gly Leu Glu Arg Ile Asn Thr Arg Arg Asn Ile Gln Leu Tyr Asn
        420                 425                 430
Val Asp Asn Thr Arg Ile Leu Lys Thr Thr Tyr His Ser Ser Asn Ile
        435                 440                 445
Ser Asn Thr Asp Tyr Leu Arg Leu Ala Val Glu Asp Phe Tyr Thr Cys
450                 455                 460
Gln Ser Ile Tyr Arg Glu Glu Leu Lys Gly Leu Glu Arg Trp Val Val
465                 470                 475                 480
Glu Asn Lys Leu Asp Gln Leu Lys Phe Ala Arg Gln Lys Thr Ala Tyr
            485                 490                 495
Cys Tyr Phe Ser Val Ala Ala Thr Leu Ser Ser Pro Glu Leu Ser Asp
        500                 505                 510
Ala Arg Ile Ser Trp Ala Lys Asn Gly Ile Leu Thr Thr Val Val Asp
        515                 520                 525
Asp Phe Phe Asp Ile Gly Gly Thr Ile Asp Glu Leu Thr Asn Leu Ile
        530                 535                 540
Gln Cys Val Glu Lys Trp Asn Val Asp Val Asp Lys Asp Cys Cys Ser
545                 550                 555                 560
Glu His Val Arg Ile Leu Phe Leu Ala Leu Lys Asp Ala Ile Cys Trp
            565                 570                 575
Ile Gly Asp Glu Ala Phe Lys Trp Gln Ala Arg Asp Val Thr Ser His
        580                 585                 590
Val Ile Gln Thr Trp Leu Glu Leu Met Asn Ser Met Leu Arg Glu Ala
```

```
                      595                 600                 605
Ile Trp Thr Arg Asp Ala Tyr Val Pro Thr Leu Asn Glu Tyr Met Glu
610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
                660                 665                 670

Asp Ile His Ser Phe Lys Arg Glu Phe Lys Glu Gly Lys Leu Asn Ala
                675                 680                 685

Val Ala Leu His Leu Ser Asn Gly Glu Ser Gly Lys Val Glu Glu Glu
            690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
                740                 745                 750

Asn Asp Asp Gly Phe Thr Gly Asn Thr Ile Leu Asp Thr Val Lys Asp
                755                 760                 765

Ile Ile Tyr Asn Pro Leu Val Leu Val Asn Asn Glu Glu Gln Arg
                770                 775                 780
```

<210> SEQ ID NO 5
<211> LENGTH: 513
<212> TYPE: PRT
<213> ORGANISM: Stevia rebaudiana

<400> SEQUENCE: 5

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
            35                  40                  45

Arg Val Pro Glu Val Pro Gly Val Pro Leu Leu Gly Asn Leu Leu Gln
        50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190
```

-continued

```
Arg Lys Ile Phe Gln Ser Glu Leu Phe Gly Leu Ala Met Arg Gln Ala
            195                 200                 205

Leu Gly Lys Asp Val Glu Ser Leu Tyr Val Asp Leu Lys Ile Thr
    210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Val Asn Thr Ile Gly
                485                 490                 495

Leu Thr Thr Gln Met Leu Arg Pro Leu Arg Ala Ile Ile Lys Pro Arg
            500                 505                 510

Ile
```

<210> SEQ ID NO 6
<211> LENGTH: 476
<212> TYPE: PRT
<213> ORGANISM: Stevia rebaudiana

<400> SEQUENCE: 6

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45
```

```
Ala Gly Trp Asp Ser Glu Pro Glu Arg Phe Val Arg Glu Arg Ile Lys
    50                  55                  60
Lys His Gly Ser Pro Leu Val Phe Lys Thr Ser Leu Phe Gly Asp Arg
 65                  70                  75                  80
Phe Ala Val Leu Cys Gly Pro Ala Gly Asn Lys Phe Leu Phe Cys Asn
                 85                  90                  95
Glu Asn Lys Leu Val Ala Ser Trp Trp Pro Val Pro Val Arg Lys Leu
            100                 105                 110
Phe Gly Lys Ser Leu Leu Thr Ile Arg Gly Asp Glu Ala Lys Trp Met
            115                 120                 125
Arg Lys Met Leu Leu Ser Tyr Leu Gly Pro Asp Ala Phe Ala Thr His
        130                 135                 140
Tyr Ala Val Thr Met Asp Val Val Thr Arg Arg His Ile Asp Val His
145                 150                 155                 160
Trp Arg Gly Lys Glu Glu Val Asn Val Phe Gln Thr Val Lys Leu Tyr
                165                 170                 175
Ala Phe Glu Leu Ala Cys Arg Leu Phe Met Asn Leu Asp Asp Pro Asn
            180                 185                 190
His Ile Ala Lys Leu Gly Ser Leu Phe Asn Ile Phe Leu Lys Gly Ile
        195                 200                 205
Ile Glu Leu Pro Ile Asp Val Pro Gly Thr Arg Phe Tyr Ser Ser Lys
210                 215                 220
Lys Ala Ala Ala Ile Arg Ile Glu Leu Lys Lys Leu Ile Lys Ala
225                 230                 235                 240
Arg Lys Leu Glu Leu Lys Glu Gly Lys Ala Ser Ser Ser Gln Asp Leu
                245                 250                 255
Leu Ser His Leu Leu Thr Ser Pro Asp Glu Asn Gly Met Phe Leu Thr
            260                 265                 270
Glu Glu Glu Ile Val Asp Asn Ile Leu Leu Leu Leu Phe Ala Gly His
        275                 280                 285
Asp Thr Ser Ala Leu Ser Ile Thr Leu Leu Met Lys Thr Leu Gly Glu
290                 295                 300
His Ser Asp Val Tyr Asp Lys Val Leu Lys Glu Gln Leu Glu Ile Ser
305                 310                 315                 320
Lys Thr Lys Glu Ala Trp Glu Ser Leu Lys Trp Glu Asp Ile Gln Lys
                325                 330                 335
Met Lys Tyr Ser Trp Ser Val Ile Cys Glu Val Met Arg Leu Asn Pro
            340                 345                 350
Pro Val Ile Gly Thr Tyr Arg Glu Ala Leu Val Asp Ile Asp Tyr Ala
        355                 360                 365
Gly Tyr Thr Ile Pro Lys Gly Trp Lys Leu His Trp Ser Ala Val Ser
370                 375                 380
Thr Gln Arg Asp Glu Ala Asn Phe Glu Asp Val Thr Arg Phe Asp Pro
385                 390                 395                 400
Ser Arg Phe Glu Gly Ala Gly Pro Thr Pro Phe Thr Phe Val Pro Phe
                405                 410                 415
Gly Gly Gly Pro Arg Met Cys Leu Gly Lys Glu Phe Ala Arg Leu Glu
            420                 425                 430
Val Leu Ala Phe Leu His Asn Ile Val Thr Asn Phe Lys Trp Asp Leu
        435                 440                 445
Leu Ile Pro Asp Glu Lys Ile Glu Tyr Asp Pro Met Ala Thr Pro Ala
450                 455                 460
Lys Gly Leu Pro Ile Arg Leu His Pro His Gln Val
```

```
465                 470                 475
```

<210> SEQ ID NO 7
<211> LENGTH: 717
<212> TYPE: PRT
<213> ORGANISM: Taxus cuspidate

<400> SEQUENCE: 7

```
Met Gln Ala Asn Ser Asn Thr Val Glu Gly Ala Ser Gln Gly Lys Ser
1               5                   10                  15

Leu Leu Asp Ile Ser Arg Leu Asp His Ile Phe Ala Leu Leu Leu Asn
            20                  25                  30

Gly Lys Gly Gly Asp Leu Gly Ala Met Thr Gly Ser Ala Leu Ile Leu
        35                  40                  45

Thr Glu Asn Ser Gln Asn Leu Met Ile Leu Thr Thr Ala Leu Ala Val
    50                  55                  60

Leu Val Ala Cys Val Phe Phe Val Trp Arg Arg Gly Gly Ser Asp
65                  70                  75                  80

Thr Gln Lys Pro Ala Val Arg Pro Thr Pro Leu Val Lys Glu Glu Asp
                85                  90                  95

Glu Glu Glu Glu Asp Asp Ser Ala Lys Lys Val Thr Ile Phe Phe
            100                 105                 110

Gly Thr Gln Thr Gly Thr Ala Glu Gly Phe Ala Lys Ala Leu Ala Glu
        115                 120                 125

Glu Ala Lys Ala Arg Tyr Glu Lys Ala Val Phe Lys Val Val Asp Leu
    130                 135                 140

Asp Asn Tyr Ala Ala Asp Glu Gln Tyr Glu Lys Leu Lys Lys
145                 150                 155                 160

Glu Lys Leu Ala Phe Phe Met Leu Ala Thr Tyr Gly Asp Gly Glu Pro
                165                 170                 175

Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
        195                 200                 205

Asn Arg Gln Tyr Glu His Phe Asn Lys Val Ala Lys Ala Val Asp Glu
    210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Asp Phe Thr Ala Trp Arg Glu Gln
                245                 250                 255

Val Trp Pro Glu Leu Asp Gln Leu Leu Arg Asp Glu Asp Glu Pro
            260                 265                 270

Thr Ser Ala Thr Pro Tyr Thr Ala Ala Ile Pro Glu Tyr Arg Val Glu
        275                 280                 285

Ile Tyr Asp Ser Val Val Ser Val Tyr Glu Glu Thr His Ala Leu Lys
    290                 295                 300

Gln Asn Gly Gln Ala Val Tyr Asp Ile His His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
            340                 345                 350

Gly Asp His Val Gly Val His Thr Glu Asn Ser Ile Glu Thr Val Glu
        355                 360                 365
```

Glu Ala Ala Lys Leu Leu Gly Tyr Gln Leu Asp Thr Ile Phe Ser Val
370                 375                 380

His Gly Asp Lys Glu Asp Gly Thr Pro Leu Gly Gly Ser Ser Leu Pro
385                 390                 395                 400

Pro Pro Phe Pro Gly Pro Cys Thr Leu Arg Thr Ala Leu Ala Arg Tyr
                405                 410                 415

Ala Asp Leu Leu Asn Pro Pro Arg Lys Ala Ala Phe Leu Ala Leu Ala
            420                 425                 430

Ala His Ala Ser Asp Pro Ala Glu Ala Glu Arg Leu Lys Phe Leu Ser
            435                 440                 445

Ser Pro Ala Gly Lys Asp Glu Tyr Ser Gln Trp Val Thr Ala Ser Gln
450                 455                 460

Arg Ser Leu Leu Glu Ile Met Ala Glu Phe Pro Ser Ala Lys Pro Pro
465                 470                 475                 480

Leu Gly Val Phe Phe Ala Ala Ile Ala Pro Arg Leu Gln Pro Arg Tyr
                485                 490                 495

Tyr Ser Ile Ser Ser Ser Pro Arg Phe Ala Pro Ser Arg Ile His Val
                500                 505                 510

Thr Cys Ala Leu Val Tyr Gly Pro Ser Pro Thr Gly Arg Ile His Lys
                515                 520                 525

Gly Val Cys Ser Asn Trp Met Lys Asn Ser Leu Pro Ser Glu Glu Thr
530                 535                 540

His Asp Cys Ser Trp Ala Pro Val Phe Val Arg Gln Ser Asn Phe Lys
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
                580                 585                 590

Glu Ala Gly Glu Lys Leu Gly Pro Ala Val Leu Phe Phe Gly Cys Arg
                595                 600                 605

Asn Arg Gln Met Asp Tyr Ile Tyr Glu Asp Glu Leu Lys Gly Tyr Val
                610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
                645                 650                 655

Thr Trp Ser Leu Ile Ala Gln Gly Gly Tyr Leu Tyr Val Cys Gly Asp
                660                 665                 670

Ala Lys Gly Met Ala Arg Asp Val His Arg Thr Leu His Thr Ile Val
                675                 680                 685

Gln Glu Gln Glu Ser Val Asp Ser Ser Lys Ala Glu Phe Leu Val Lys
690                 695                 700

Lys Leu Gln Met Asp Gly Arg Tyr Leu Arg Asp Ile Trp
705                 710                 715

<210> SEQ ID NO 8
<211> LENGTH: 710
<212> TYPE: PRT
<213> ORGANISM: Stevia rebaudiana

<400> SEQUENCE: 8

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
                20                  25                  30

-continued

```
Asp Pro Thr Thr Leu Pro Ala Leu Lys Met Leu Val Glu Asn Arg Glu
         35                  40                  45
Leu Leu Thr Leu Phe Thr Thr Ser Phe Ala Val Leu Ile Gly Cys Leu
 50                  55                  60
Val Phe Leu Met Trp Arg Arg Ser Ser Lys Lys Leu Val Gln Asp
 65                  70                  75                  80
Pro Val Pro Gln Val Ile Val Lys Lys Glu Lys Ser Glu
                     85                  90                  95
Val Asp Asp Gly Lys Lys Val Ser Ile Phe Tyr Gly Thr Gln Thr
                 100                 105                 110
Gly Thr Ala Glu Gly Phe Ala Lys Ala Leu Val Glu Ala Lys Val
             115                 120                 125
Arg Tyr Glu Lys Thr Ser Phe Lys Val Ile Asp Leu Asp Asp Tyr Ala
         130                 135                 140
Ala Asp Asp Asp Glu Tyr Glu Glu Lys Leu Lys Lys Glu Ser Leu Ala
145                 150                 155                 160
Phe Phe Phe Leu Ala Thr Tyr Gly Asp Gly Glu Pro Thr Asp Asn Ala
                 165                 170                 175
Ala Asn Phe Tyr Lys Trp Phe Thr Glu Gly Asp Asp Lys Gly Glu Trp
             180                 185                 190
Leu Lys Lys Leu Gln Tyr Gly Val Phe Gly Leu Gly Asn Arg Gln Tyr
         195                 200                 205
Glu His Phe Asn Lys Ile Ala Ile Val Val Asp Lys Leu Thr Glu
     210                 215                 220
Met Gly Ala Lys Arg Leu Val Pro Val Gly Leu Gly Asp Asp Asp Gln
225                 230                 235                 240
Cys Ile Glu Asp Asp Phe Thr Ala Trp Lys Glu Leu Val Trp Pro Glu
                 245                 250                 255
Leu Asp Gln Leu Leu Arg Asp Glu Asp Asp Thr Ser Val Thr Thr Pro
             260                 265                 270
Tyr Thr Ala Ala Val Leu Glu Tyr Arg Val Val Tyr His Asp Lys Pro
         275                 280                 285
Ala Asp Ser Tyr Ala Glu Asp Gln Thr His Thr Asn Gly His Val Val
     290                 295                 300
His Asp Ala Gln His Pro Ser Arg Ser Asn Val Ala Phe Lys Lys Glu
305                 310                 315                 320
Leu His Thr Ser Gln Ser Asp Arg Ser Cys Thr His Leu Glu Phe Asp
                 325                 330                 335
Ile Ser His Thr Gly Leu Ser Tyr Glu Thr Gly Asp His Val Gly Val
             340                 345                 350
Tyr Ser Glu Asn Leu Ser Glu Val Val Asp Glu Ala Leu Lys Leu Leu
         355                 360                 365
Gly Leu Ser Pro Asp Thr Tyr Phe Ser Val His Ala Asp Lys Glu Asp
     370                 375                 380
Gly Thr Pro Ile Gly Gly Ala Ser Leu Pro Pro Phe Pro Pro Cys
385                 390                 395                 400
Thr Leu Arg Asp Ala Leu Thr Arg Tyr Ala Asp Val Leu Ser Ser Pro
                 405                 410                 415
Lys Lys Val Ala Leu Leu Ala Leu Ala Ala His Ala Ser Asp Pro Ser
             420                 425                 430
Glu Ala Asp Arg Leu Lys Phe Leu Ala Ser Pro Ala Gly Lys Asp Glu
         435                 440                 445
```

-continued

```
Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
690                 695                 700

Tyr Leu Arg Asp Val Trp
705             710

<210> SEQ ID NO 9
<211> LENGTH: 473
<212> TYPE: PRT
<213> ORGANISM: Stevia rebaudiana

<400> SEQUENCE: 9

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Phe Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Gln Tyr Leu Lys
                85                  90                  95

Lys Ala Val Asp Gly Leu Gln Pro Glu Val Thr Arg Phe Leu Glu Gln
            100                 105                 110
```

His Ser Pro Asp Trp Ile Ile Tyr Asp Phe Thr His Tyr Trp Leu Pro
            115                 120                 125

Ser Ile Ala Ala Ser Leu Gly Ile Ser Arg Ala Tyr Phe Cys Val Ile
        130                 135                 140

Thr Pro Trp Thr Ile Ala Tyr Leu Ala Pro Ser Ser Asp Ala Met Ile
145                 150                 155                 160

Asn Asp Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Met Glu Pro Tyr Glu Ala Pro Gly Ile Ser Asp Gly Tyr Arg
        195                 200                 205

Met Gly Met Val Phe Lys Gly Ser Asp Cys Leu Leu Phe Lys Cys Tyr
210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Leu Phe Gly
370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Asn Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
450                 455                 460

Arg Ala Val Ala Ile Asp His Glu Ser
465                 470

<210> SEQ ID NO 10
<211> LENGTH: 468
<212> TYPE: PRT
<213> ORGANISM: Stevia rebaudiana

<400> SEQUENCE: 10

Met Pro Ile Ser Asp Ile Asn Ala Gly Ser His Ile Leu Val Phe Pro

```
1               5                   10                  15
Tyr Pro Ala Gln Gly His Met Leu Thr Leu Leu Asp Leu Thr His Gln
                20                  25                  30

Leu Ala Ile Arg Asn Leu Thr Ile Thr Ile Leu Val Thr Pro Lys Asn
                35                  40                  45

Leu Pro Thr Ile Ser Pro Leu Leu Ala Ala His Pro Thr Thr Val Ser
 50                      55                  60

Ala Leu Leu Leu Pro Leu Pro Pro His Pro Ala Ile Pro Ser Gly Ile
 65                  70                  75                  80

Glu Asn Val Lys Asp Leu Pro Asn Asp Ala Phe Lys Ala Met Met Val
                 85                  90                  95

Ala Leu Gly Asp Leu Tyr Asn Pro Leu Arg Asp Trp Phe Arg Asn Gln
                100                 105                 110

Pro Asn Pro Pro Val Ala Ile Ile Ser Asp Phe Phe Leu Gly Trp Thr
            115                 120                 125

His His Leu Ala Val Glu Leu Gly Ile Arg Arg Tyr Thr Phe Ser Pro
        130                 135                 140

Ser Gly Ala Leu Ala Leu Ser Val Ile Phe Ser Leu Trp Arg Tyr Gln
145                 150                 155                 160

Pro Lys Arg Ile Asp Val Glu Asn Glu Lys Glu Ala Ile Lys Phe Pro
                165                 170                 175

Lys Ile Pro Asn Ser Pro Glu Tyr Pro Trp Trp Gln Leu Ser Pro Ile
            180                 185                 190

Tyr Arg Ser Tyr Val Glu Gly Asp Pro Asp Ser Glu Phe Ile Lys Asp
        195                 200                 205

Gly Phe Leu Ala Asp Ile Ala Ser Trp Gly Ile Val Ile Asn Ser Phe
    210                 215                 220

Thr Glu Leu Glu Gln Val Tyr Val Asp His Leu Lys His Glu Leu Gly
225                 230                 235                 240

His Asp Gln Val Phe Ala Val Gly Pro Leu Leu Pro Pro Gly Asp Lys
                245                 250                 255

Thr Ser Gly Arg Gly Gly Ser Ser Ser Asn Asp Val Leu Ser Trp Leu
            260                 265                 270

Asp Thr Cys Ala Asp Arg Thr Val Val Tyr Val Cys Phe Gly Ser Gln
        275                 280                 285

Met Val Leu Thr Asn Gly Gln Met Glu Val Val Ala Leu Gly Leu Glu
    290                 295                 300

Lys Ser Arg Val Lys Phe Val Trp Ser Val Lys Glu Pro Thr Val Gly
305                 310                 315                 320

His Glu Ala Ala Asn Tyr Gly Arg Val Pro Pro Gly Phe Glu Asp Arg
                325                 330                 335

Val Ser Gly Arg Gly Leu Val Ile Arg Gly Trp Val Pro Gln Val Ala
            340                 345                 350

Ile Leu Ser His Asp Ser Val Gly Val Phe Leu Thr His Cys Gly Trp
        355                 360                 365

Asn Ser Val Met Glu Ala Val Ala Ala Glu Val Leu Met Leu Thr Trp
    370                 375                 380

Pro Met Ser Ala Asp Gln Phe Ser Asn Ala Thr Leu Leu His Glu Leu
385                 390                 395                 400

Lys Val Gly Ile Lys Val Cys Glu Gly Ser Asn Ile Val Pro Asn Ser
                405                 410                 415

Asp Glu Leu Ala Glu Leu Phe Ser Lys Ser Leu Ser Asp Glu Thr Arg
            420                 425                 430
```

```
Leu Glu Arg Lys Arg Val Lys Glu Phe Ala Lys Ser Ala Lys Glu Ala
            435                 440                 445

Val Gly Pro Lys Gly Ser Ser Val Gly Glu Leu Glu Arg Leu Val Asp
    450                 455                 460

Asn Leu Ser Leu
465

<210> SEQ ID NO 11
<211> LENGTH: 460
<212> TYPE: PRT
<213> ORGANISM: Stevia rebaudiana

<400> SEQUENCE: 11

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65              70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
```

```
              325                 330                 335
Cys Lys Gln Leu Asp Val Leu Ala His Glu Ser Val Gly Cys Phe Val
            340                 345                 350
Thr His Cys Gly Phe Asn Ser Thr Leu Glu Ala Ile Ser Leu Gly Val
        355                 360                 365
Pro Val Val Ala Met Pro Gln Phe Ser Asp Gln Thr Thr Asn Ala Lys
    370                 375                 380
Leu Leu Asp Glu Ile Leu Gly Val Gly Val Arg Val Lys Ala Asp Glu
385                 390                 395                 400
Asn Gly Ile Val Arg Arg Gly Asn Leu Ala Ser Cys Ile Lys Met Ile
                405                 410                 415
Met Glu Glu Glu Arg Gly Val Ile Ile Arg Lys Asn Ala Val Lys Trp
            420                 425                 430
Lys Asp Leu Ala Lys Val Ala Val His Glu Gly Gly Ser Ser Asp Asn
        435                 440                 445
Asp Ile Val Glu Phe Val Ser Glu Leu Ile Lys Ala
    450                 455                 460

<210> SEQ ID NO 12
<211> LENGTH: 495
<212> TYPE: PRT
<213> ORGANISM: Stevia rebaudiana

<400> SEQUENCE: 12

Met Ser Pro Lys Met Val Ala Pro Pro Thr Asn Leu His Phe Val Leu
1               5                   10                  15
Phe Pro Leu Met Ala Gln Gly His Leu Val Pro Met Val Asp Ile Ala
            20                  25                  30
Arg Ile Leu Ala Gln Arg Gly Ala Thr Val Thr Ile Ile Thr Thr Pro
        35                  40                  45
Tyr His Ala Asn Arg Val Arg Pro Val Ile Ser Arg Ala Ile Ala Thr
    50                  55                  60
Asn Leu Lys Ile Gln Leu Leu Glu Leu Gln Leu Arg Ser Thr Glu Ala
65                  70                  75                  80
Gly Leu Pro Glu Gly Cys Glu Ser Phe Asp Gln Leu Pro Ser Phe Glu
                85                  90                  95
Tyr Trp Lys Asn Ile Ser Thr Ala Ile Asp Leu Leu Gln Gln Pro Ala
            100                 105                 110
Glu Asp Leu Leu Arg Glu Leu Ser Pro Pro Asp Cys Ile Ile Ser
        115                 120                 125
Asp Phe Leu Phe Pro Trp Thr Thr Asp Val Ala Arg Arg Leu Asn Ile
130                 135                 140
Pro Arg Leu Val Phe Asn Gly Pro Gly Cys Phe Tyr Leu Leu Cys Ile
145                 150                 155                 160
His Val Ala Ile Thr Ser Asn Ile Leu Gly Glu Asn Glu Pro Val Ser
                165                 170                 175
Ser Asn Thr Glu Arg Val Val Leu Pro Gly Leu Pro Asp Arg Ile Glu
            180                 185                 190
Val Thr Lys Leu Gln Ile Val Gly Ser Ser Arg Pro Ala Asn Val Asp
        195                 200                 205
Glu Met Gly Ser Trp Leu Arg Ala Val Glu Ala Glu Lys Ala Ser Phe
    210                 215                 220
Gly Ile Val Val Asn Thr Phe Glu Glu Leu Glu Pro Glu Tyr Val Glu
225                 230                 235                 240
```

```
Glu Tyr Lys Thr Val Lys Asp Lys Lys Met Trp Cys Ile Gly Pro Val
            245                 250                 255

Ser Leu Cys Asn Lys Thr Gly Pro Asp Leu Ala Glu Arg Gly Asn Lys
        260                 265                 270

Ala Ala Ile Thr Glu His Asn Cys Leu Lys Trp Leu Asp Glu Arg Lys
            275                 280                 285

Leu Gly Ser Val Leu Tyr Val Cys Leu Gly Ser Leu Ala Arg Ile Ser
        290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
370                 375                 380

Ala Gly Val Pro Met Ile Thr Trp Pro Phe Phe Ala Asp Gln Phe Leu
385                 390                 395                 400

Asn Glu Ala Phe Ile Val Glu Val Leu Lys Ile Gly Val Arg Ile Gly
                405                 410                 415

Val Glu Arg Ala Cys Leu Phe Gly Glu Asp Lys Val Gly Val Leu
            420                 425                 430

Val Lys Lys Glu Asp Val Lys Lys Ala Val Glu Cys Leu Met Asp Glu
        435                 440                 445

Asp Glu Asp Gly Asp Gln Arg Arg Lys Arg Val Ile Glu Leu Ala Lys
        450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495

<210> SEQ ID NO 13
<211> LENGTH: 454
<212> TYPE: PRT
<213> ORGANISM: Stevia rebaudiana

<400> SEQUENCE: 13

Met Ser Leu Lys Gly Asn Asp Lys Glu Leu His Leu Val Met Phe Pro
1               5                   10                  15

Phe Phe Ala Phe Gly His Ile Thr Pro Phe Val Gln Leu Ser Asn Lys
            20                  25                  30

Ile Ser Ser Leu Tyr Pro Gly Val Lys Ile Thr Phe Leu Ala Ala Ser
        35                  40                  45

Ala Ser Val Ser Arg Ile Glu Thr Met Leu Asn Pro Ser Thr Asn Thr
    50                  55                  60

Lys Val Ile Pro Leu Thr Leu Pro Arg Val Asp Gly Leu Pro Glu Gly
65                  70                  75                  80

Val Glu Asn Thr Ala Asp Ala Ser Pro Ala Thr Ile Gly Leu Leu Val
                85                  90                  95

Val Ala Ile Asp Leu Met Gln Pro Gln Ile Lys Thr Leu Leu Ala Asn
            100                 105                 110

Leu Lys Pro Asp Phe Val Ile Phe Asp Phe Val His Trp Trp Leu Pro
        115                 120                 125
```

Glu Ile Ala Ser Glu Leu Gly Ile Lys Thr Ile Tyr Phe Ser Val Tyr
      130                 135                 140

Met Ala Asn Ile Val Met Pro Ser Thr Ser Lys Leu Thr Gly Asn Lys
145                 150                 155                 160

Pro Ser Thr Val Glu Asp Ile Lys Ala Leu Gln Gln Ser Asp Gly Ile
                165                 170                 175

Pro Val Lys Thr Phe Glu Ala Ile Ser Leu Met Asn Val Phe Lys Ser
            180                 185                 190

Phe His Asp Trp Met Asp Lys Cys Ile Asn Gly Cys Asn Leu Met Leu
        195                 200                 205

Ile Lys Ser Cys Arg Glu Met Glu Gly Ser Arg Ile Asp Asp Val Thr
210                 215                 220

Lys Gln Ser Thr Arg Pro Val Phe Leu Ile Gly Pro Val Val Pro Glu
225                 230                 235                 240

Pro His Ser Gly Glu Leu Asp Glu Thr Trp Ala Asn Trp Leu Asn Arg
                245                 250                 255

Phe Pro Ala Lys Ser Val Ile Tyr Cys Ser Phe Gly Ser Glu Thr Phe
            260                 265                 270

Leu Thr Asp Asp Gln Ile Arg Glu Leu Ala Leu Gly Leu Glu Leu Thr
        275                 280                 285

Gly Leu Pro Phe Phe Leu Val Leu Asn Phe Pro Ala Asn Val Asp Lys
290                 295                 300

Ser Ala Glu Leu Lys Arg Thr Leu Pro Asp Gly Phe Leu Glu Arg Val
305                 310                 315                 320

Lys Asp Lys Gly Ile Val His Ser Gly Trp Val Gln Gln Arg His Ile
                325                 330                 335

Leu Ala His Asp Ser Val Gly Cys Tyr Val Phe His Ala Gly Tyr Gly
            340                 345                 350

Ser Val Ile Glu Gly Leu Val Asn Asp Cys Gln Leu Val Met Leu Pro
        355                 360                 365

Met Lys Val Asp Gln Phe Thr Asn Ser Lys Val Ile Ala Leu Glu Leu
370                 375                 380

Lys Ala Gly Val Glu Val Asn Arg Arg Asp Glu Asp Gly Tyr Phe Gly
385                 390                 395                 400

Lys Asp Asp Val Phe Glu Ala Val Glu Ser Val Met Met Asp Thr Glu
                405                 410                 415

Asn Glu Pro Ala Lys Ser Ile Arg Glu Asn His Arg Lys Leu Lys Glu
            420                 425                 430

Phe Leu Gln Asn Asp Glu Ile Gln Lys Lys Tyr Ile Ala Asp Phe Val
        435                 440                 445

Glu Asn Leu Lys Ala Leu
    450

<210> SEQ ID NO 14
<211> LENGTH: 473
<212> TYPE: PRT
<213> ORGANISM: Stevia rebaudiana

<400> SEQUENCE: 14

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser

```
            35                  40                  45
Thr Thr Arg Asn Ile Gln Arg Leu Ser Ser His Ile Ser Pro Leu Ile
 50                  55                  60
Asn Val Val Gln Leu Thr Leu Pro Arg Val Gln Glu Leu Pro Glu Asp
 65                  70                  75                  80
Ala Glu Ala Thr Thr Asp Val His Pro Glu Asp Ile Pro Tyr Leu Lys
                 85                  90                  95
Lys Ala Ser Asp Gly Leu Gln Pro Glu Val Thr Arg Phe Leu Glu Gln
                100                 105                 110
His Ser Pro Asp Trp Ile Ile Tyr Asp Tyr Thr His Tyr Trp Leu Pro
                115                 120                 125
Ser Ile Ala Ala Ser Leu Gly Ile Ser Arg Ala His Phe Ser Val Thr
                130                 135                 140
Thr Pro Trp Ala Ile Ala Tyr Met Gly Pro Ser Ala Asp Ala Met Ile
145                 150                 155                 160
Asn Gly Ser Asp Gly Arg Thr Thr Val Glu Asp Leu Thr Thr Pro Pro
                165                 170                 175
Lys Trp Phe Pro Phe Pro Thr Lys Val Cys Trp Arg Lys His Asp Leu
                180                 185                 190
Ala Arg Leu Val Pro Tyr Lys Ala Pro Gly Ile Ser Asp Gly Tyr Arg
                195                 200                 205
Met Gly Leu Val Leu Lys Gly Ser Asp Cys Leu Leu Ser Lys Cys Tyr
                210                 215                 220
His Glu Phe Gly Thr Gln Trp Leu Pro Leu Leu Glu Thr Leu His Gln
225                 230                 235                 240
Val Pro Val Val Pro Val Gly Leu Leu Pro Pro Glu Val Pro Gly Asp
                245                 250                 255
Glu Lys Asp Glu Thr Trp Val Ser Ile Lys Lys Trp Leu Asp Gly Lys
                260                 265                 270
Gln Lys Gly Ser Val Val Tyr Val Ala Leu Gly Ser Glu Val Leu Val
                275                 280                 285
Ser Gln Thr Glu Val Val Glu Leu Ala Leu Gly Leu Glu Leu Ser Gly
                290                 295                 300
Leu Pro Phe Val Trp Ala Tyr Arg Lys Pro Lys Gly Pro Ala Lys Ser
305                 310                 315                 320
Asp Ser Val Glu Leu Pro Asp Gly Phe Val Glu Arg Thr Arg Asp Arg
                325                 330                 335
Gly Leu Val Trp Thr Ser Trp Ala Pro Gln Leu Arg Ile Leu Ser His
                340                 345                 350
Glu Ser Val Cys Gly Phe Leu Thr His Cys Gly Ser Gly Ser Ile Val
                355                 360                 365
Glu Gly Leu Met Phe Gly His Pro Leu Ile Met Leu Pro Ile Phe Gly
                370                 375                 380
Asp Gln Pro Leu Asn Ala Arg Leu Leu Glu Asp Lys Gln Val Gly Ile
385                 390                 395                 400
Glu Ile Pro Arg Asn Glu Glu Asp Gly Cys Leu Thr Lys Glu Ser Val
                405                 410                 415
Ala Arg Ser Leu Arg Ser Val Val Glu Lys Glu Gly Glu Ile Tyr
                420                 425                 430
Lys Ala Asn Ala Arg Glu Leu Ser Lys Ile Tyr Asn Asp Thr Lys Val
                435                 440                 445
Glu Lys Glu Tyr Val Ser Gln Phe Val Asp Tyr Leu Glu Lys Asn Thr
                450                 455                 460
```

Arg Ala Val Ala Ile Asp His Glu Ser
465                 470

<210> SEQ ID NO 15
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 15

Gly Ser Thr Gly Ser
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 16

Met Ala Leu Leu Leu Ala Val Phe
1               5

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 17
cggcatatga gttttgatat tgccaaatac ccg                              33

<210> SEQ ID NO 18
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 18
cggctagctt atgccagcca ggccttgatt ttg                              33

<210> SEQ ID NO 19
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 19
cgcggctagc gaaggagata tacatatgca aacggaacac gtcattttat tg         52

<210> SEQ ID NO 20
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 20
cggaattcgc tcacaacccc ggcaaatgtc gg                               32

```
<210> SEQ ID NO 21
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 21
gcgaattcga aggagatata catatggcaa ccactcattt ggatgtttg            49

<210> SEQ ID NO 22
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 22
gcgctcgagt catttgttg ccttaatgag tagcgcc                          37

<210> SEQ ID NO 23
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 23
taaaccatgg gttttgatat tgccaaatac ccg                             33

<210> SEQ ID NO 24
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 24
cggggtacct catttgttg ccttaatgag tagcgc                           36

<210> SEQ ID NO 25
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 25
cggctcgagt catttgttg ccttaatgag tagcgc                           36

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 26
cgtaaccggt gcctctgcta accatgttca tgccttc                         37

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 27
ctccttcgct agcttatgcc agcc       24

<210> SEQ ID NO 28
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 28
cgtagaattc agaaggagat atacatatgt tgatttcaa tgaatatatg aaaagtaagg    60
c       61

<210> SEQ ID NO 29
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 29
gatggtcgac tcacaactga cgaaacgcaa tgtaatc    37

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
accatggctc tgtctctgtg catt    24

<210> SEQ ID NO 31
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 31
tctcgagtta acgttgttct tcgttttcg    29

<210> SEQ ID NO 32
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 32
actcgagaag aaggagatat acatatgaag actgg    35

<210> SEQ ID NO 33
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 33
tgaattctca gattacgatt tcaaatactt tgg    33

<210> SEQ ID NO 34
<211> LENGTH: 91
<212> TYPE: DNA
<213> ORGANISM: Artificial Sequence
<220> FEATURE:
<223> OTHER INFORMATION: Synthetic oligonucleotide

<400> SEQUENCE: 34
gacgctcgag gagcaataac tagcataacc ccttggggcc tctaaacggg tcttgagggg    60 tttttttgctt gtgtaggctg gagctgcttc g                                  91

<210> SEQ ID NO 35
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 35
gacgagtact gaacgtcgga attgatccgt cgac                                34

<210> SEQ ID NO 36
<211> LENGTH: 91
<212> TYPE: DNA
<213> ORGANISM: Artificial Sequence
<220> FEATURE:
<223> OTHER INFORMATION: Synthetic oligonucleotide

<400> SEQUENCE: 36
gacggagctc gagcaataac tagcataacc ccttggggcc tctaaacggg tcttgagggg    60 tttttttgctt gtgtaggctg gagctgcttc g                                  91

<210> SEQ ID NO 37
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 37
atgacgattt ttgataatta tgaagtgtgg tttgtcattg cattaattgc gttgcgctca    60
ctg                                                                  63

<210> SEQ ID NO 38
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 38
atgacgattt ttgataatta tgaagtgtgg tttgtcattg gcatccgctt acagacaagc    60
tgtg                                                                 64

<210> SEQ ID NO 39
<211> LENGTH: 64
<212> TYPE: DNA
<213> ORGANISM: Artificial Sequence

```
<220> FEATURE:
<223> OTHER INFORMATION: Synthetic oligonucleotide

<400> SEQUENCE: 39
ttagcgacga aacccgtaat acacttcgtt ccagcgcagc cgacgtcgga attgatccgt      60
cgac                                                                   64
```

US 9,284,570 B2

MICROBIAL PRODUCTION OF NATURAL SWEETENERS, DITERPENOID STEVIOL GLYCOSIDES

RELATED APPLICATIONS

This application claims priority to U.S. Provisional Application No. 61/418,357, filed on Nov. 30, 2010, which is hereby incorporated by reference in its entirety. This application also claims the benefit of U.S. application Ser. No. 13/249,388, filed Sep. 30, 2011, which is hereby incorporated by reference in its entirety.

GOVERNMENT INTEREST

This work was funded in part by the National Institutes of Health under Grant Number 1-R01-GM085323-01A1. The government has certain rights in this invention.

FIELD OF THE INVENTION

The invention relates to the production of one or more terpenoids, including steviol and steviol glycosides, through genetic engineering.

BACKGROUND OF THE INVENTION

Steviol glycosides are natural constituents of the plant *Stevia rebaudiana* Bertoni, referred to as *Stevia*. *Stevia* is native to the Amambay region of Northeastern Paraguay and has been reported to grow in neighboring parts of Brazil and Argentina. Although *Stevia* continues to be a rare plant in its native habitat, it is now farmed in South America and Asia. *Stevia* leaves have been used to sweeten beverages and make tea. In addition, the leaves are also used for their medicinal benefits in high blood pressure, obesity, topical dressing of wounds and other skin disorders (1).

The crushed *Stevia* leaves are about 30 times sweeter than sugar (2). The sweet tasting components of the *Stevia* plant are called steviol glycosides. Steviol glycosides are obtained from the leaves of *Stevia rebaudiana* Bertoni. The leaves are processed with hot water and aqueous extraction to concentrate and purify the steviol glycosides. The final product may be spray dried. Steviol glycosides preparations are available as white or slightly yellowish white crystalline odorless soluble powders.

SUMMARY OF THE INVENTION

The current production of steviol glycoside sweeteners solely relies on cultivation of the plant *Stevia* and extraction of steviol glycosides from the plant, which yields variable mixtures with undesirable taste profiles, and the yield is severely limited by cultivation and extraction procedures. A promising solution to this problem is to engineer fast growing microorganisms such as bacteria and yeast to synthesize steviol glycosides or its precursor molecule steviol that can be chemically converted to steviol glycosides through established inexpensive methods.

Aspects of the present invention relate to methods involving recombinantly expressing a copalyl diphosphate synthase (CPS), kaurene synthase (KS) and a geranylgeranyl diphosphate to synthase (GGPPS) enzyme in a cell that expresses (or overexpresses one or more components of) an endogenous isopenoid synthesis pathway, such as the non-mevalonate (MEP) pathway or the mevalonic acid pathway (MVA). In some embodiments the cell is a bacterial cell such as an *Escherichia coli* cell. In some embodiments, the bacterial cell is a Gram-positive cell such as a *Bacillus* cell. In some embodiments, the cell is a yeast cell such as a *Saccharomyces* cell, *Pichia* cell, or a *Yarrowia* cell. In some embodiments, the cell is an algal cell or a plant cell.

In some embodiments, the copalyl diphosphate synthase (CPS) enzyme is a *Stevia* enzyme such as a *Stevia rebaudiana* Bertoni enzyme. In some embodiments, the kaurene synthase (KS) enzyme is a *Stevia* enzyme such as a *Stevia rebaudiana* Bertoni enzyme. In some embodiments, the GGPPS enzyme is a *Taxus* enzyme such as a *Taxus canadenis* enzyme or *Stevia* enzyme such as a *Stevia rebaudiana* Bertoni enzyme. In some embodiments, the gene encoding the copalyl diphosphate synthase (CPS) enzyme and/or the gene encoding the kaurene synthase (KS) enzyme and/or the gene encoding the GGPPS enzyme and/or the genes encoding the one or more components of the MEP pathway is/are expressed from one or more plasmids. In some embodiments, the gene encoding the copalyl diphosphate synthase (CPS) enzyme and/or the gene encoding the kaurene synthase (KS) enzyme and/or the gene encoding the GGPPS enzyme and/or the genes encoding the one or more components of the MEP pathway is/are incorporated into the genome of the cell.

In some embodiments, one or more overexpressed components of the non-mevalonate (MEP) pathway are selected from dxs, ispC, ispD, ispE, ispF, ispG, ispH, idi, ispA and ispB. In certain embodiments, dxs, idi, ispD and ispF are overexpressed in the cell. For example, dxs, idi, ispD and ispF can be expressed or overexpressed on the operon dxs-idi-iSpDF, or ispC, ispE, ispG and ispH can be expressed or overexpressed on the operon ispC-ispE-ispG-ispH. In some embodiments, the gene encoding the copalyl diphosphate synthase (CPS) enzyme, the gene encoding the kaurene synthase (KS) enzyme and the gene encoding the GGPPS enzyme are expressed together on an operon. In some embodiments, the operon is KS-CPS-GGPPS.

In some embodiments, the cell further expresses a kaurene oxidase (KO), a P450 mono-oxygenase, and kaurenoic acid 13-hydroxylase (KAH), a cytochrome P450, or a catalytically active portion thereof. In certain embodiments, the KO and KAH enzyme or a catalytically active portion thereof is fused to a cytochrome P450 reductase enzyme or a catalytically active portion thereof. In some embodiments, the gene encoding the kaurene oxidase (KO) enzyme or catalytically active portion thereof or fusion thereof to a cytochrome P450 reductase enzyme or a catalytically active portion, and the gene encoding the kaurenoic acid 13-hydroxylase (KAH) enzyme or catalytically active portion thereof or fusion thereof to a cytochrome P450 reductase enzyme or a catalytically active portion, are expressed together on an operon. In some embodiments, the operon is KO-KAH.

In some embodiments, the gene encoding the kaurene oxidase (KO) synthase enzyme, the gene encoding the kaurenoic acid 13-hydroxylase (KAH) enzyme and/or the gene encoding the catalytically active portion thereof fused to a cytochrome P450 reductase enzyme or a catalytically active portion is expressed from one or more plasmids. In some embodiments, the gene encoding the kaurene oxidase (KO) synthase enzyme, the gene encoding the kaurenoic acid 13-hydroxylase (KAH) enzyme and/or the gene encoding the catalytically active portion thereof fused to a cytochrome P450 reductase enzyme or a catalytically active portion is incorporated into the genome of the cell.

In some embodiments, the cell further expresses one or more UDP-glycosyltransferases (UGTs) or a catalytically active portion thereof. In some embodiments, the UDP-glycosyltransferase (UGT) enzyme(s) is a *Stevia* enzyme such as a *Stevia rebaudiana* Bertoni enzyme. In some embodiments, the gene encoding for one or more of the UDP-glycosyltransferases (UGTs) or a catalytically active portion are expressed together on an operon. In some embodiments, the gene encoding for the UDP-glycosyltransferases (UGTs) or a catalytically active portion is expressed from one or more plasmids. In some embodiments, the gene encoding for the UDP-glycosyltransferases (UGTs) or a catalytically active portion is incorporated into the genome of the cell.

The expression of the copalyl diphosphate synthase (CPS), kaurene synthase (KS), a geranylgeranyl diphosphate synthase (GGPPS) enzyme, and the one or more components of the MEP pathway can be balanced to maximize production of kaurene. Methods associated with the invention can further encompass culturing a cell to produce kaurene.

The expression of the copalyl diphosphate synthase (CPS), kaurene synthase (KS), a geranylgeranyl diphosphate synthase (GGPPS), kaurene oxidase (KO) enzyme, kaurenoic acid 13-hydroxylase (KAH) enzyme and/or catalytically active portion of KO and KAH fused to a cytochrome P450 reductase enzyme, and the one or more components of the MEP pathway, can be balanced to maximize production of steviol. Methods associated with the invention can further encompass culturing a cell to produce steviol.

Methods associated with the invention can further comprise recovering the kaurene, steviol or steviol glycosides from the cell culture. In some embodiments, the kaurene, steviol and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside D, rebaudioside E, rebaudioside F, and dulcoside A. In some embodiments, the terpenoid produced is steviobioside or stevioside.

Aspects of the invention relate to cells that express or overexpress an endogenous isoprenoid synthesis pathway, such as MEP or MVA (or are engineered to overexpress one or more components of said pathway), and that recombinantly expresses a copalyl diphosphate synthase (CPS), kaurene synthase (KS), a geranylgeranyl diphosphate synthase (GGPPS) enzyme, kaurene oxidase (KO) enzyme, kaurenoic acid 13-hydroxylase (KAH) enzyme and/or catalytically active portion of KO and KAH fused to a cytochrome P450 reductase enzyme. In some embodiments the cell is a bacterial cell such as an *Escherichia coli* cell, and which overexpresses one or more components of the MEP pathway as described in detail herein. In some embodiments, the bacterial cell is a Gram-positive cell such as a *Bacillus* cell. In some embodiments, the cell is a yeast cell such as a *Saccharomyces* cell, *Pichia pastoris*, or a *Yarrowia* cell. In some embodiments, the cell is an algal cell or a plant cell.

Aspects of the invention relate to methods for selecting a cell that exhibits enhanced production of kaurene, steviol or steviol glycosides, including creating or obtaining a cell that expresses or overexpresses one or more components of the mevalonic acid pathway (MVA) or non-mevalonate (MEP) pathway, producing kaurene, steviol or steviol glycosides from the cell, comparing the amount of kaurene, steviol or steviol glycosides produced from the cell to the amount of kaurene, steviol or steviol glycosides produced in a control cell, and selecting a first improved cell that produces a higher amount of kaurene, steviol or steviol glycosides than a control cell, wherein a first improved cell that produces a higher amount of kaurene, steviol or steviol glycosides than the control cell is a cell that exhibits enhanced production of kaurene, steviol or steviol glycosides. In some embodiments, the steviol or steviol glycoside is steviobioside, stevioside, rebaudioside A, rebaudioside B, rebaudioside C, rebaudioside D, rebaudioside E, rebaudioside F, or dulcoside A.

In some embodiments, the cell recombinantly expresses a copalyl diphosphate synthase (CPS) enzyme and/or a kaurene synthase (KS) enzyme and/or a geranylgeranyl diphosphate to synthase (GGPPS) enzyme. Methods can further comprise altering the level of expression of one or more of the components of the non-mevalonate (MEP) pathway, the copalyl diphosphate synthase (CPS) enzyme, the kaurene synthase (KS) enzyme and/or the geranylgeranyl diphosphate synthase (GGPPS) enzyme in the first improved cell to produce a second improved cell, and comparing the amount of kaurene produced from the second improved cell to the amount of kaurene produced in the first improved cell, wherein a second improved cell that produces a higher amount of kaurene than the first improved cell is a cell that exhibits enhanced production of kaurene. In some embodiments, the copalyl diphosphate synthase (CPS) and/or the kaurene synthase (KS) enzyme is a *Stevia* enzyme, optionally a *Stevia rebaudiana* Bertoni enzyme. The cell can further recombinantly express any of the polypeptides associated with the invention.

Aspects of the invention relate to isolated polypeptides comprising a kaurene oxidase (KO) enzyme, kaurenoic acid 13-hydroxylase (KAH) enzyme or a catalytically active portion of KO or KAH fused to a cytochrome P450 reductase enzyme or a catalytically active portion thereof. In some embodiments, the cytochrome P450 reductase enzyme is a Taxus cytochrome P450 reductase (TCPR). In certain embodiments, the kaurene oxidase (KO) enzyme or kaurenoic acid 13-hydroxylase (KAH) enzyme and TCPR are joined by a linker such as GSTGS (SEQ ID NO:15). In some embodiments, the kaurene oxidase (KO) enzyme, kaurenoic acid 13-hydroxylase (KAH) enzyme or TCPR are truncated to remove all or part of the transmembrane region. In some embodiments, an additional peptide is fused to kaurene oxidase (KO) enzyme and/or kaurenoic acid 13-hydroxylase (KAH). In certain embodiments, the additional peptide is from bovine 17α hydroxylase. In certain embodiments, the peptide is MALLLAVF (SEQ ID NO:16). Aspects of the invention also encompass nucleic acid molecules that encode any of the polypeptides associated with the invention and cells that recombinantly express any of the polypeptides associated with the invention.

Aspects of the invention relate to methods for increasing terpenoid production in a cell that produces one or more terpenoids, such as kaurene, steviol or steviol glycosides. The methods include controlling the accumulation of indole in the cell or in a culture of the cells, thereby increasing terpenoid production in a cell. Any of the cells described herein can be used in the methods, including bacterial cells, such as *Escherichia coli* cells; Gram-positive cells, such as *Bacillus* cells; yeast cells, such as *Saccharomyces cells, Pichia* cells, or *Yarrowia* cells; algal cells; plant cells; and any of the engineered cells described herein.

In some embodiments, the step of controlling the accumulation of indole in the cell or in a culture of the cells includes balancing the upstream non-mevalonate isoprenoid pathway with the downstream product synthesis pathways and/or modifying or regulating the indole pathway. In other embodiments, the step of controlling the accumulation of indole in the cell or in a culture of the cells includes or further includes removing the accumulated indole from the fermentation through chemical methods, such as by using absorbents or scavengers.

Aspects of the invention relate to methods that include measuring the amount or concentration of indole in a cell that produces one or more terpenoids, such as kaurene, steviol or steviol glycosides, or in a culture of the cells that produce one or more terpenoids, such as kaurene, steviol or steviol glycosides. The methods can include measuring the amount or concentration of indole two or more times. In some embodiments, the measured amount or concentration of indole in the cell or cells is used to guide a process of producing one or more terpenoids. In some embodiments, the measured amount or concentration of indole is used to guide strain construction.

In other aspects, the invention provides a method for making a product containing a terpenoid selected from kaurene, a steviol, or a steviol glycoside. The method comprises increasing terpenoid production in a cell that produces one or more terpenoids by controlling the accumulation of indole in the cell or in a culture of the cells. The terpenoid is recovered from the cell(s), and optionally, one or more chemical or enzymatic steps may be performed to produce the desired compound. The recovered terpenoid or the terpenoid prepared through one or more chemical or enzymatic steps, is incorporated into a product to thereby make the product containing a terpenoid. In various embodiments, the product is a food product or beverage. These and other aspects of the invention, as well as various embodiments thereof, will become more apparent in reference to the drawings and detailed description of the invention.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE INVENTION

Figure 1:
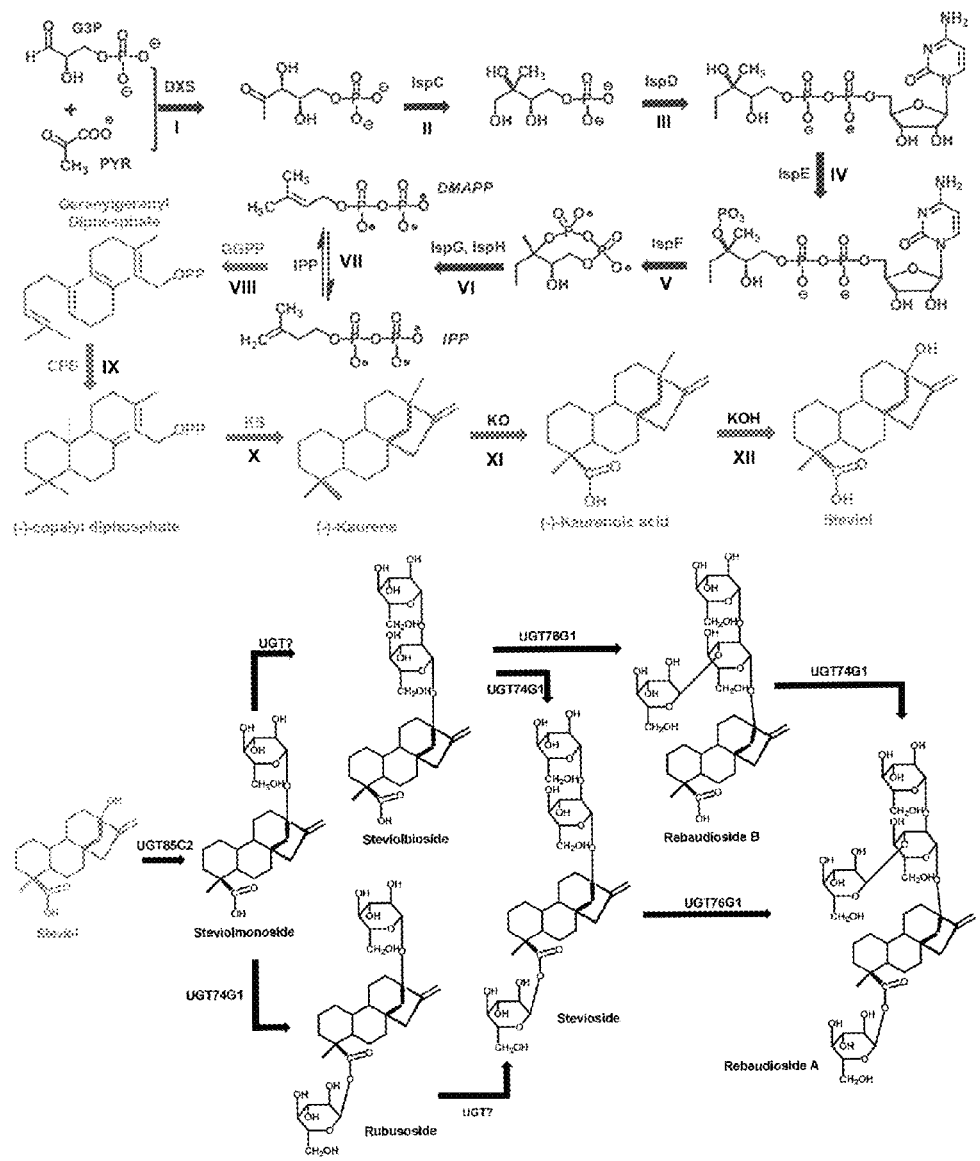
FIG. 1. Biosynthetic scheme for steviol glycoside production. Schematics of the four modules, the native, upstream isoprenoid pathway (steps I to VII), synthetic downstream kaurene (steps VIII to X), steviol (steps XI and XII), and steviol glycoside (bottom panel). In the biosynthetic network, divergence of the MEP isoprenoid pathway from glycolysis initiates at the precursors glyceraldehyde-3 phosphate (G3P) and pyruvate (PYR) (I-VII). The steviol pathway bifurcation starts from the *E. coli* isoprenoid precursor IPP and DMAPP to the "linear" precursor geranylgeranyl diphosphate (VIII), copalyl diphosphate (CP) (IX), "cyclic" karuene (X), "oxidized" kaurenoic acid (XI), and steviol (XII), followed by multiple rounds of glycosylations to steviol glycosides. The enzymes involved in the biosynthetic pathways from G3P and PYR to steviol glycosides include: DXS-1-deoxy-D-xylulose-5-phosphate synthase, ispC-1-Deoxy-D-xylulose-5-phosphate reductoisomerase, IspD-4-diphosphocytidyl-2C-methyl-D-erythritol synthase, IspE-4-diphosphocytidyl-2-C-methyl-D-erythritol kinase, IspF-2C-Methyl-D-erythritol-2,4-cyclodiphosphate Synthase, IspG-1-hydroxy-2-methyl-2-(E)-butenyl-4-diphosphate synthase, IspH-4-hydroxy-3-methyl-2-(E)-butenyl-4-diphosphate reductase, IDI-isopentenyl-diphosphate isomerase, GGPPS-geranyl geranyldiphosphate synthase, CPS-copalyl diphosphate synthase, KS-kaurene synthase, KO-kaurene oxidase, KAH-kaurenoic acid 13-hydroxylase, and UGT-UDP-glycosyltransferases.

Steviol glycosides are of recent immense interest to the food and beverages industry due to their intense sweetening properties and as a potential alternative to synthetic sweeteners. *Stevia* leaves accumulate a mixture of at least eight steviol glycosides. Here, we describe a multivariate-modular approach to metabolic pathway engineering for the production of steviol or steviol in engineered cells including bacterial cells such as *Escherichia coli* and yeast such as *Saccharomyces cerevisiae*.

Unless recited in a claim, this invention as claimed is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The worldwide demand for high potency sweeteners is increasing, and with blending of different sweeteners becoming a standard practice, the demand and supply for alternatives such as pure steviol glycoside is expected to increase. Developing technology for the production of high purity steviol glycosides such as Rebaudioside A (Reb A) would have significant changes on the political and socio economics of current non-caloric sweetener use in food and beverages (F&B) industry (3). Recently, Coca-Cola company released the details of the production of high purity Reb A from plant extracted steviol glycoside mixture following food grade specifications and GMP manufacturing for human consumption (4). Clinical, biochemical and metabolic studies support Reb A as general purpose-sweetener for human consumption (5). This is reflected in the recent FDA approval for Reb A as GRAS for use as general purpose sweetener in food and beverages industry. The featured markets and uses for this molecule are (i) soft drinks and cordials; (ii) milk, soy and mineral drinks; (iii) canned fruit, jams and juices; (iv) ice creams, yoghurts, and other dietary products; (v) cakes, biscuits, pastries and desserts; (vi) sugar to free beers and alcoholic beverages; (vii) toppings, sauces, chutneys, spreads, etc. and; (viii) cereals, muesli bars and confectionaries (3).

Thus Reb A is a high value chemical in the multibillion dollar F&B industry. Developing a sustainable and economical production process for Reb A not only has commercial interest but also potential health implications, due to the extensive history of use as a natural herbal sweetener and medicine.

Stevia leaves accumulate a mixture of at least eight steviol glycosides. The details of major steviol glycosides characterized from the Stevia are shown in Table 1. The diversity of various steviol glycosides results from the differences in the glycosylation on the diterpenoid skeleton, steviol, which primarily determines the sweetening property of these molecules. Stevioside is the main sweetening compound found in the Stevia leaf (2-10%), followed by Reb A (~1-3%) (1). Stevioside and Reb A were tested for stability in carbonated beverages and found to be both heat and pH stable.

TABLE 1

Details of steviol glycosides characterized from Stevia rebaudiana Bertoni leaf

| | Compound name | R1 (glycosylation at C13—OH) | R2 (glycosylation at C19—COOH) |
|---|---|---|---|
| 1 | Steviolbioside | H | β-Glc-β-Glc(2→1) |
| 2 | Stevioside | β-Glc | β-Glc-β-Glc(2→1) |
| 3 | rebaudioside A | β-Glc | β-Glc-β-Glc(2→1)<br>\|<br>β-Glc(3→1) |
| 4 | rebaudioside B | H | β-Glc-β-Glc(2→1)<br>\|<br>β-Glc(3→1) |
| 5 | rebaudioside C | β-Glc | β-Glc-α-Rha(2→1)<br>\|<br>β-Glc(3→1) |
| 6 | rebaudioside D | β-Glc-β-Glc(2→1) | β-Glc-β-Glc(2→1)<br>\|<br>β-Glc(3→1) |
| 7 | rebaudioside E | β-Glc-β-Glc(2→1) | β-Glc-β-Glc(2→1) |
| 8 | rebaudioside F | β-Glc | β-Glc-β-Xyl(2→1)<br>\|<br>β-Glc(3→1) |
| 9 | dulcoside A | β-Glc | β-Glc-α-Rha(2→1) |

The sweetening properties of Stevia extract are derived from stevioside and Reb A molecules. Stevioside is reported to be 143 times sweeter than sucrose on a weight basis and Reb A is 242 times sweeter (1). However the taste quality of Reb A is better than stevioside, because it is sweeter and less bitter. Thus in the natural extract the taste "quality" is determined by the percentage composition of stevioside and Reb A. If stevioside is more than 50%, the taste is "common/traditional" with a "licorice" aftertaste, whereas if Reb A is more than 50%, the taste is improved with a reduced aftertaste (2). Thus developing high Reb A steviol glycosides is important for its use as sweeteners. However, the extraction and purification from plant leaf is technically challenging due to (i) low accumulation (2-10 wt %), (ii) production of steviol glycosides depends on the cultivation method and climate, and (iii) the difficulty in extracting Reb A from a mixture of structurally similar steviol glycosides.

Recent developments in metabolic engineering and synthetic biology offer new possibilities for the overproduction of complex natural products such as steviol glycosides through more technically amenable microbial hosts (6, 7). Steviol glycosides are diterpenoids and the early biosynthetic pathway until GGPP share common intermediates with other diterpenoid such as Taxol biosynthetic pathway (8). Similar to Taxol biosynthesis, the overall pathway is modularized into parts: 1) the formation of starting precursor IPP and DMAPP from the central carbon metabolites glyceraldehydes-3-phosphate and pyruvate (FIG. 1, blue to structures); 2) the production of the first dedicated intermediate, kaurene (FIG. 1, red structures); 3) biosynthesis of the key intermediate, steviol (FIG. 1, gray structures); and 4) the formation various steviol glycosides (FIG. 1, black structures).

In plants, the formation of common isoprenoid precursor IPP and DMAPP can be derived from two biosynthetic routes, the MVA and MEP pathway. The first step in the diterpenoid steviol biosynthesis is conversion of IPP and DMAPP into GGPP. GGPP is the four subunit precursor for all diterpenoid molecules. Next, the cyclization of the GGPP, first by protonation-initiated cyclization to copalyl diphosphate (CDP) is catalyzed by CDP synthase (CPS). Kaurene is then produced from CDP by an ionization dependant cyclization catalysed by kaurene synthase (KS). These enzymes have been identified and characterized from the native biosynthetic pathway in Stevia (8).

Kaurene is then oxidized in a three step reaction to kaurenoic acid, by kaurene oxidase (KO) a P450 mono-oxygenase. A full length KO cDNA was expressed in yeast and demonstrated that it could convert kaurene to kaurenoic acid. The next step in the pathway is the hydroxylation of kaurenoic acid by kaurenoic acid 13-hydroxylase (KAH). KAH, a cytochrome P450, was expressed in yeast and converted kaurenoic acid to steviol (9).

Aglycone steviol has two hydroxyl groups, one attached to the C-19 of the C-4 carboxyl and the other attached to the C-13, both of which in theory can be glycosylated using UDP-glycosyltransferases (UGTs) (10). In vitro enzyme studies using 13-O- and 19-O-methylsteviol as substrates found that only 19-O-steviol could serve as a substrate and concluded that synthesis of steviol glycosides starts with the glucosylation of the 13-hydroxyl of steviol, which produces steviolmonoside. The next step is the glucosylation of the C-20 of the 13-O-glucose of steviolmonoside, which results in the production of steviolbioside. Stevioside is then produced by the glycosylation of the C-19 carboxyl of steviolbioside. In vitro studies on various substrates shows that C-19 is glucosylated after the glucosylation of the C2' of the C13-glucose of steviolmonoside.

Reb A is then synthesized by glucosylation of the C-3' of the C-13-O-glucose. Further, no product was observed using Reb A as a substrate, indicating it is the terminal step in the pathway. The tri-glycoside stevioside and the tetra-glycoside Reb A typically represent the majority of the steviol glycosides present in Stevia leaves. In addition to these, rhamnosylated glycosides can also be formed by addition of a UDP rhamnose moiety to steviolmonoside, and in genotypes enriched in Reb A C, the C2' of the C13-glucose can be xylosylated to form rebaudioside F.

The detailed understanding and characterization of biochemical pathways for steviol glycosides and the recent advancements in engineering of the upstream isoprenoid pathway to reroute the IPP and DMAPP through heterologous biosynthetic pathway engineering provides the basis for directed, heterologous production of steviol glycosides in a convenient microbial-based bioprocess. There are nine steps in the pathway for the biosynthesis of Reb A of which one glycosylation remains unidentified.

As mentioned above, the current Stevia-based production and purification present significant challenges to reduce production costs. Our proposed synthetic route using heterologous pathways that have been reconstructed through amenable microbial hosts offers superior opportunities for improving current production schemes and to generate new derivatives of steviosides which are not naturally occurring. In addition, the microbial systems lend themselves to metabolic engineering efforts through a combination of genetic manipulations and bioprocess engineering to continually improve production capabilities. Taken together, the above provide several compelling reasons to reconstitute the Reb A biosynthesis through simpler microbial hosts.

The metabolic pathway for steviol glycosides consists of an upstream isoprenoid pathway that is native to *E. coli* and a heterologous downstream terpenoid pathway (FIG. 1). The upstream mevalonic acid (MVA) pathway in certain microbial organisms such as yeast or methylerythritol phosphate (MEP) pathway in certain microbial organisms such as *E. coli* can produce the two common building blocks, isopentenyl pyrophosphate (IPP) and dimethylallyl pyrophosphate (DMAPP), from which isoprenoid compounds are formed (7).

Microbial production of terpenoids such as kaurene and steviol is demonstrated herein. When expressed at satisfactory levels, microbial routes reduce dramatically the cost of production of such compounds. Additionally, they utilize cheap, abundant and renewable feedstocks (such as sugars and other carbohydrates) and can be the source for the synthesis of numerous derivatives that may exhibit far superior properties than the original compound. A key element in the cost-competitive production of compounds of the isoprenoid pathway using a microbial route is the amplification of this pathway in order to allow the overproduction of these molecules.

Described herein are methods and compositions for optimizing production of terpenoids in cells by controlling expression of genes or proteins participating in an upstream pathway and a downstream pathway. The upstream pathway involves production of isopentyl pyrophosphate (IPP) and dimethylallyl pyrophosphate (DMAPP), which can be achieved by two different metabolic pathways: the mevalonic acid (MVA) pathway and the MEP (2-C-methyl-D-erythritol 4-phosphate) pathway, also called the MEP/DOXP (2-C-methyl-D-erythritol 4-phosphate/1-deoxy-D-xylulose 5-phosphate) pathway, the non-mevalonate pathway or the mevalonic acid-independent pathway.

The downstream pathway is a synthetic pathway that leads to production of a terpenoids and involves recombinant gene expression of a terpenoid synthase (also referred to as terpene cyclase) enzyme, and a geranylgeranyl diphosphate synthase (GGPPS) enzyme. In some embodiments, a terpenoid synthase enzyme is a diterpenoid synthase enzyme. Several non-limiting examples of diterpenoid synthase enzymes include copalyl diphosphate synthase (CPS) and kaurene synthase (KS).

The optimization of terpenoid synthesis by manipulation of the upstream and downstream pathways described herein is not a simple linear or additive process. Rather, through complex combinatorial analysis, optimization is achieved through balancing components of the upstream and downstream pathways.

Aspects of the invention relate to controlling the expression of genes and proteins in the MEP pathway for optimized production of a terpenoid. Optimized production of a terpenoid refers to producing a higher amount of a terpenoid following pursuit of an optimization strategy than would be achieved in the absence of such a strategy. It should be appreciated that any gene and/or protein within the MEP pathway is encompassed by methods and compositions described herein. In some embodiments, a gene within the MEP pathway is one of the following: dxs, ispC, ispD, ispE, ispF, ispG, ispH, idi, ispA or ispB. Expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway.

It should be appreciated that genes and/or proteins can be regulated alone or in combination. For example, the expression of dxs can be upregulated or downregulated alone or in combination with upregulation or downregulation of expression of one or more of ispC, ispD, ispE, ispF, ispG, ispH, idi, ispA and ispB. The expression of ispC can be upregulated or downregulated alone or in combination with upregulation or downregulation of expression of one or more of dxs, ispD, ispE, ispF, ispG, ispH, idi, ispA and ispB. The expression of ispD can be upregulated or downregulated alone or in combination with upregulation or downregulation of expression of one or more of dxs, ispC, ispE, ispF, ispG, ispH, idi, ispA and ispB. The expression of ispE can be upregulated or downregulated alone or in combination with upregulation or downregulation of expression of one or more of dxs, ispC, ispD, ispF, ispG, ispH, idi, ispA and ispB. The expression of ispF can be upregulated or downregulated alone or in combination with upregulation or downregulation of expression of one or more of dxs, ispC, ispD, ispE, ispG, ispH, idi, ispA and ispB. The expression of ispG can be upregulated or downregulated alone or in combination with upregulation or downregulation of expression of one or more of dxs, ispC, ispD, ispE, ispF, ispH, idi, ispA and ispB. The expression of ispH can be upregulated or downregulated alone or in combination with upregulation or downregulation of expression of one or more of dxs, ispC, ispD, ispE, ispF, ispG, idi, ispA and ispB. The expression of idi can be upregulated or downregulated alone or in combination with upregulation or downregulation of expression of one or more of dxs, ispC, ispD, ispE, ispF, ispG, ispH, ispA and ispB. The expression of ispA can be upregulated or downregulated alone or in combination with upregulation or downregulation of expression of one or more of dxs, ispC, ispD, ispE, ispF, ispG, ispH, idi and ispB. The expression of ispB can be upregulated or downregulated alone or in combination with upregulation or downregulation of expression of one or more of dxs, ispC, ispD, ispE, ispF, ispG, ispH, idi and ispA. In some embodiments, expression of the gene and/or protein of one or more of dxs, ispC, ispD, ispE, ispF, ispG, ispH, and idi is upregulated while expression of the gene and/or protein of ispA and/or ispB is downregulated.

Expression of genes within the MEP pathway can be regulated in a modular method. As used herein, regulation by a modular method refers to regulation of multiple genes together. For example, in some embodiments, multiple genes within the MEP pathway are recombinantly expressed on a contiguous region of DNA, such as an operon. It should be appreciated that a cell that expresses such a module can also express one or more other genes within the MEP pathway either recombinantly or endogenously.

A non-limiting example of a module of genes within the MEP pathway is a module containing the genes dxs, idi, ispD and ispF, referred to herein as dxs-idi-ispDF. It should be appreciated that modules of genes within the MEP pathway, consistent with aspects of the invention, can contain any of the genes within the MEP pathway, in any order.

Expression of genes and proteins within the downstream synthetic terpenoid synthesis pathway can also be regulated in order to optimize terpenoid production. The synthetic downstream terpenoid synthesis pathway involves recombinant expression of a terpenoid synthase enzyme and a GGPPS enzyme. Any terpenoid synthase enzyme, as discussed above, can be expressed with GGPPS depending on the downstream product to be produced. For example, CPS and KS is used for the production of kaurene. Recombinant expression of the CPS and KS enzyme and the GGPPS enzyme can be regulated independently or together. In some embodiments the three enzymes are regulated together in a modular fashion. For example the three enzymes can be expressed in an operon in any order (e.g., GGPPS-CPS-KS, referred to as "GCK," or KS-CPS-GGPPS, referred to as "KCG" or KS-GGPPS-CPS, referred to as "KGC" or GGPPS-KS-CPS, referred to as "GKC").

The synthetic downstream steviol synthesis pathway also involves recombinant expression of P450 mono-oxygenases such as kaurene oxidase (KO) and kaurenoic acid 13-hydroxylase (KAH) enzyme. Any P450 mono-oxygenases, as discussed above, can be expressed with CPS and KS synthase enzyme and the GGPPS enzyme on the downstream product to be produced. For example, kaurene oxidase (KO) and kaurenoic acid 13-hydroxylase (KAH) enzyme are used for the production of steviol from kaurene. Recombinant expression of the kaurene oxidase (KO) and kaurenoic acid 13-hydroxylase (KAH) enzyme and/or a gene encoding for a catalytically active portion thereof is fused to a cytochrome P450 reductase enzyme (CPR) (to form KOCPR and KAHCPR fusions) or a catalytically active portion can be regulated independently or together. In some embodiments these two enzymes are regulated together in a modular fashion. For example the two enzymes can be expressed in an operon in either order (KOCPR-KAHCPR, or KAHCPR-KOCPR).

Manipulation of the expression of genes and/or proteins, including modules such as the dxs-idi-ispDF operon, the GGPPS-CPS-KS operon, and the KOCPR-KAHCPR operon, can be achieved through various methods. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell. For example, in certain embodiments, a strain containing an additional copy of the dxs-idi-ispDF operon on its chromosome under Trc promoter control produces an increased amount of taxadiene relative to one overexpressing only the synthetic downstream pathway. In some embodiments, expression of genes or operons can be regulated through manipulating the order of the genes within a module. For example, in certain embodiments, changing the order of the genes in a downstream synthetic operon from GCK to KCG or KGC or GKC and KOCPR-KAHCPR to KAHCPR-KOCPR results in an increase in steviol production. In some embodiments, expression of genes or operons is regulated through integration of one or more genes or operons into a chromosome. For example, in certain embodiments, integration of the upstream dxs-idi-ispDF operon into the chromosome of a cell results in increased production.

In some embodiments, the dxs-idi-ispD-ispF operon and the K-C-G operon are controlled by the same promoter, such as the T7 promoter, or promoters of similar strength.

It should be appreciated that the genes associated with the invention can be obtained from a variety of sources. In some embodiments, the genes within the MEP pathway are bacterial genes such as *Escherichia coli* genes. In some embodiments, the gene encoding for GGPPS is a plant gene. For example, the gene encoding for GGPPS can be from a species of *Taxus* such as *Taxus canadensis* (*T. canadensis*) or *Stevia* such as *Stevia rebaudiana* Bertoni. In some embodiments, the gene encoding for CPS and/or KS synthase is a plant gene. For example, the gene encoding for CPS and KS synthase can be from a species of *Stevia* such as *Stevia rebaudiana* Bertoni. Representative GenBank Accession numbers for *T. canadensis* GGPPS, *Stevia rebaudiana* GGPPS, CPS and KS are provided by AF081514, ABD92926, AAB87091, and AF097311_1 respectively, the sequences of which are incorporated by reference herein in their entireties. Exemplary protein sequences for a number of the enzymes described herein are provided in Table 2.

As one of ordinary skill in the art would be aware, homologous genes for use in methods associated with the invention can be obtained from other species and can be identified by homology searches, for example through a protein BLAST search, available at the National Center for Biotechnology Information (NCBI) internet site (www.ncbi.nlm.nih.gov). Genes and/or operons associated with the invention can be cloned, for example by PCR amplification and/or restriction digestion, from DNA from any source of DNA which contains the given gene. In some embodiments, a gene and/or operon associated with the invention is synthetic. Any to means of obtaining a gene and/or operon associated with the invention is compatible with the instant invention.

In some embodiments, further optimization of terpenoid production is achieved by modifying a gene before it is recombinantly expressed in a cell. In some embodiments, the GGPPS enzyme has one or more of the follow mutations: A162V, G140C, L182M, F218Y, D160G, C184S, K367R, A151T, M185I, D264Y, E368D, C184R, L331I, G262V, R365S, A114D, S239C, G295D, I276V, K343N, P183S, I172T, D267G, I149V, T234I, E153D and T259A (wherein the numbering refers to amino acids of *T. canadensis* GGPPS [see GenBank accession numbers AF081514 and AAD16018]; residues at equivalent positions of other GGPPS enzymes can likewise be mutated). In some embodiments, the GGPPS enzyme has a mutation in residue S239 and/or residue G295. In certain embodiments, the GGPPS enzyme has the mutation S239C and/or G295D.

In some embodiments, modification of a gene before it is recombinantly expressed in a cell involves codon optimization for expression in a bacterial cell. Codon usages for a variety of organisms can be accessed in the Codon Usage Database (www.kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene before it is recombinantly expressed in a cell involves making one or more mutations in the gene before it is recombinantly expressed in a cell. For example, a mutation can involve a substitution or deletion of a single nucleotide or multiple nucleotides. In some embodiments, a mutation of one or more nucleotides in a gene will result in a mutation in the protein produced from the gene, such as a substitution or deletion of one or more amino acids. Such modifications are made using standard molecular biology methods well known in the art.

In some embodiments, it may be advantageous to use a cell that has been optimized for production of a terpenoid. For example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. For example, copy numbers of components at rate-limiting steps in to the MEP pathway such as (dxs, ispD, ispF, idi) can be amplified, such as by additional episomal expression.

In some embodiments "rational design" is involved in constructing specific mutations in proteins such as enzymes. As used herein, "rational design" refers to incorporating knowledge of the enzyme, or related enzymes, such as its three dimensional structure, its active site(s), its substrate(s) and/or the interaction between the enzyme and substrate, into the design of the specific mutation. Based on a rational design approach, mutations can be created in an enzyme which can then be screened for increased production of a terpenoid relative to control levels. In some embodiments, mutations can be rationally designed based on homology modeling. As used herein, "homology modeling" refers to the process of constructing an atomic resolution model of one protein from its amino acid sequence and a three-dimensional structure of a related homologous protein.

In some embodiments, random mutations can be made in a gene, such as a gene encoding for an enzyme, and these mutations can be screened for increased production of a product, such as a terpenoid and/or steviol glycoside, relative to control levels. For example, screening for mutations in components of the MEP pathway, or components of other pathways, that lead to enhanced production of a product, such as a terpenoid and/or steviol glycoside, may be conducted through a random mutagenesis screen, or through screening of known mutations. In some embodiments, shotgun cloning of genomic fragments could be used to identify genomic regions that lead to an increase in production of a product, such as a terpenoid and/or steviol glycoside, through screening cells or organisms that have these fragments for increased production of a terpenoid. In some cases one or more mutations may be combined in the same cell or organism.

In some embodiments, production of a product, such as a terpenoid and/or steviol glycoside in a cell can be increased through manipulation of enzymes that act in the same pathway as the enzymes associated with the invention. For example, in some embodiments it may be advantageous to increase expression of an enzyme or other factor that acts upstream of a target enzyme such as an enzyme associated with the invention. This could be achieved by overexpressing the upstream factor using any of the standard methods known in the art.

Optimization of protein expression can also be achieved through selection of appropriate promoters and ribosome binding sites. In some embodiments, this may include the selection of high-copy number plasmids, or low or medium-copy number plasmids. The step of transcription to termination can also be targeted for regulation of gene expression, through the introduction or elimination of structures such as stem-loops.

Aspects of the invention relate to expression of recombinant genes in cells. The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell. It should be appreciated that some cells compatible with the invention may express an endogenous copy of one or more of the genes associated with the MEP and/or MVA pathways as well as a recombinant copy. In some embodiments, if a cell has an endogenous copy of one or more of the genes associated with the MEP or MVA pathway then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of a product, such as a terpenoid and/or steviol glycoside.

Further aspects of the invention relate to screening for bacterial cells or strains that to exhibit optimized production of a product, such as a terpenoid and/or steviol glycoside. As described above, methods associated with the invention involve generating cells that overexpress one or more genes in the MEP pathway. Terpenoid production from culturing of such cells can be measured and compared to a control cell wherein a cell that exhibits a higher amount of production of product, such as a terpenoid and/or steviol glycoside, relative to a control cell is selected as a first improved cell. The cell can be further modified by recombinant expression of a terpenoid synthase enzyme and a GGPPS enzyme. The level of expression of one or more of the components of the non-mevalonate (MEP) pathway, the terpenoid synthase enzyme and/or the GGPPS enzyme in the cell can then be manipulated and terpenoid and/or steviol glycoside production can be measured again, leading to selection of a second improved cell that produces greater amounts of product, such as a terpenoid and/or steviol glycoside, than the first improved cell. In some embodiments, the terpenoid synthase enzyme is a CPS and/or KS enzymes.

Further aspects of the invention relate to the level of accumulation of the metabolite, indole, can be controlled by genetically manipulating the microbial pathway by the overexpression, down regulation or mutation of the isoprenoid pathway genes. The metabolite indole anti-correlates as a direct variable to the diterpenoid production in engineered strains. Further controlling the accumulation of indole for improving the flux towards terpenoid biosynthesis in bacterial systems (specifically in cells, such as *E. coli* cells) or other cells, can be achieved by balancing the upstream non-mevalonate isoprenoid pathway with the downstream product synthesis pathways or by modifications to or regulation of the indole pathway. In so doing, the skilled person can reduce or control the accumulation of indole and thereby reduce the inhibitory effect of indole on the production of steviol and steviol glycosides. Other methods for reducing or controlling the accumulation of indole include removing the accumulated indole from the fermentation through chemical methods such as by using absorbents, scavengers, etc.

In other embodiments, methods are provided that include measuring the amount or concentration of indole in a cell that produces one or more terpenoids or in a culture of the cells that produce one or more terpenoids. The amount or concentration of indole can be measured once, or two or more times, as suitable, using methods known in the art and as described herein. Such methods can be used to guide processes of producing one or more terpenoids, e.g., in process improvement. Such methods can be used to guide strain construction, e.g., for strain improvement.

As demonstrated previously, by genetically engineering the non-mevalonate isoprenoid pathway in *E. coli* the accumulation of this metabolite can now be controlled which regulates the flux towards the isoprenoid biosynthesis in bacterial *E. coli* cells.

Further aspects of the invention relate to chimeric P450 enzymes. Functional expression of plant cytochrome P450 has been considered challenging due to the inherent limitations of bacterial platforms, such as the absence of electron transfer machinery, cytochrome P450 reductases, and translational incompatibility of the membrane signal modules of P450 enzymes due to the lack of an endoplasmic reticulum.

In some embodiments, the KO and KAH associated with methods of the invention is optimized through N-terminal transmembrane engineering and/or the generation of chimeric enzymes through translational fusion with a CPR redox partner. In some embodiments, the CPR redox partner is a *Stevia* cytochrome P450 reductase. In certain embodiments, the gene encoding for KO and KAH synthase can be from a species of *Stevia* such as *Stevia rebaudiana* Bertoni. Representative GenBank Accession numbers for *Stevia rebaudiana* KO and KAH are provided by ABA42921 and ACD93722, the sequence of which is incorporated by reference herein). In some embodiments, *Stevia* NADPH:cytochrome P450 reductase (SCPR) is obtained from *Stevia rebaudiana* Bertoni (GenBank Accession number ABB88839, the sequence of which is incorporated by reference herein).

The KO, KAH and TCPR (or SCPR) can be joined by a linker such as GSTGS (SEQ ID NO:15). In some embodiments, KO, KAH, TCPR and/or SCPR are truncated to remove all or part of the transmembrane region of one or both proteins. An additional peptide can also be fused to KO and KAH. For example, one or more amino acids from bovine 17a hydroxylase can be added to KO and KAH. In certain embodiments, the peptide MALLLAVF (SEQ ID NO:16) is added to KO and KAH. In certain embodiments, a chimeric enzyme constructed from the KO and SCPR is capable of carrying out the first oxidation step kaurene conversion to kaurenoic acid. In certain embodiments, a chimeric enzyme constructed from KAH and SCPR is capable of carrying out the hydroxylation step kaurenoic acid to steviol.

Further aspects of the invention relate to glycosylation of steviol on the C-4 carboxyl and to the C-13 using UDP-glycosyltransferases (UGTs). In some embodiments, the UGTs associated with methods of the invention are optimized through N-terminal transmembrane engineering and/or the generation of chimeric enzymes through domain swapping with other plant UGTs. In certain embodiments, the gene encoding for plant UGTs for the synthesis of steviol glycosides can be from a species of *Stevia* such as *Stevia rebaudiana* Bertoni. Representative GenBank Accession numbers for *Stevia rebaudiana* UGTS are provided by AAM53963, AAR06921, AAR06920, AAR06917, AAN40684, and ACE87855, the sequences of which is incorporated by reference herein.

In certain embodiments, a chimeric enzyme constructed from the UGTs is capable of carrying out the first glucosylation step steviol to steviolmonoside. In certain embodiments, a chimeric enzyme constructed from the UGTs is capable of carrying out the glucosylation of the C-20 of the 13-O-glucose of steviolmonoside, which results in the production of steviolbioside. In certain embodiments, a chimeric enzyme constructed from the UGTs is capable of carrying out the glucosylation of the glycosylation of the C-19 carboxyl of steviolbioside, which results in the production of Stevioside. In certain embodiments, a chimeric enzyme constructed from the UGTs is capable of carrying out the glucosylation of the C-3' of the C-13-O-glucose, which results in the production of Rebaudioside A (Reb A).

In some embodiments, at least one enzymatic step, such as one or more glycosylation steps, are performed ex vivo.

As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The invention also encompasses nucleic acids that encode for any of the polypeptides to described herein, libraries that contain any of the nucleic acids and/or polypeptides described herein, and compositions that contain any of the nucleic acids and/or polypeptides described herein.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired to that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (14). That heterologous DNA (14) is placed under operable control of transcriptional elements to permit the expression of the heterologous DNA in the host cell. Heterologous expression of genes associated with the invention, for production of a terpenoid, such as taxadiene, is demonstrated in the Examples section using *E. coli*. The novel method for producing terpenoids can also be expressed in other bacterial cells, fungi (including yeast cells), plant cells, etc.

A nucleic acid molecule that encodes an enzyme associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial and yeast cell. Bacterial and yeast cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of a product, such as a terpenoid and/or steviol glycoside. In some embodiments the concentration and amount of a supplemental component may be optimized. In some embodiments, how often the media is supplemented with one or more supplemental components, and the amount of time that the media is cultured before harvesting a product, such as a terpenoid and/or steviol glycoside, can be optimized.

The liquid cultures used to grow cells associated with the invention can be housed in any of the culture vessels known and used in the art. In some embodiments large scale production in an aerated reaction vessel such as a stirred tank reactor can be used to produce large quantities of product, such as a terpenoid and/or steviol glycoside, that can be recovered from the cell culture. In some embodiments, the terpenoid is recovered from the gas phase of the cell culture, for to example by adding an organic layer such as dodecane to the cell culture and recovering the terpenoid from the organic layer. In some embodiments, the terpenoid is recovered from the of the cell culture, for example by adding a polymeric resin to the cell culture and recovering the terpenoid from the polymer by solvent extraction.

Figure 2:
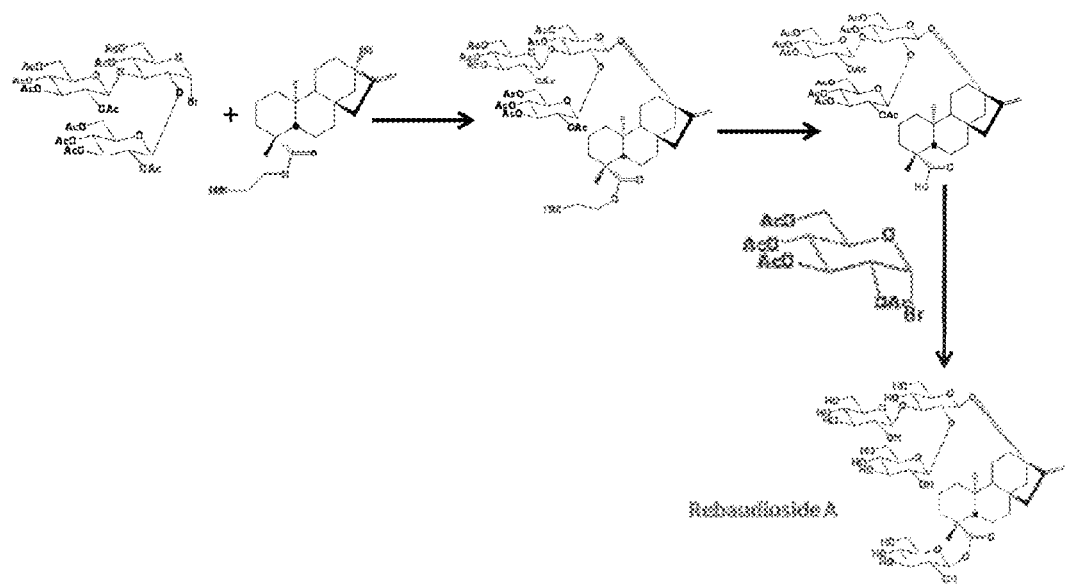
FIG. 2. Schematics of the chemical synthesis of steviol glycosides to rebaudioside A. Specifically a trimethylsilyl (TMS) protected at C19 COOH group of the steviol is synthesized from the microbially derived steviol. Further, triglucosylation at C13-OH position of the steviol is performed using protected β-Glc-β-Glc(2→1)-β-Glc(3→1) group. This is followed by a deprotection of the TMS and coupling of protected mono β-Glc-Br moiety. The final deprotection will remove all of the protecting groups to produce rebaudioside A.

The invention also encompasses the chemical synthesis for the conversion of microbially produced steviol to steviol glycosides (FIG. 2). The diterpenoid steviol can be converted to stevioside and rebaudioside A using multi-step chemical assembly of sugar moiety into steviol backbone. More specifically the chemical synthesis consists of following steps, as shown in FIG. 2. A trimethylsilyl (TMS) protected at C19 COOH group of the steviol is synthesized from the microbially derived steviol. Tri-glucosylation at the C13-OH position of the steviol is performed using protected β-Glc-β-Glc (2→1)-β-Glc(3→1) group. This is followed by a deprotection of the TMS and coupling of a protected mono β-Glc-Br moiety. The final deprotection removes all of the protecting groups to produce rebaudioside A.

In another aspect, the invention involves making a product containing a terpenoid selected from kaurene, a steviol, or a steviol glycoside. The method comprises increasing terpenoid production in a cell that produces one or more terpenoids by controlling the accumulation of indole in the cell or in a culture of the cells, and then recovering the terpenoid from the cell. The cell expresses an endogenous MVA or MEP pathway, and may overexpress one or more components of said pathway as described herein, to maximize production of kaurene, steviol, or steviol glycoside. Optionally, the method may further comprise conducting one or more chemical or enzymatic steps on the recovered terpenoid to produce a derivative of the terpenoid. The recovered terpenoid or the terpenoid prepared through one or more chemical or enzymatic steps is then incorporated into a product.

In various embodiments, the cell is a bacterial cell such as *E. coli* or *B. subtilis*, or other cell disclosed herein, including yeast (e.g., *Saccharomyces* or *Pichia pastoris*), algal and plant cells.

The step of controlling the accumulation of indole in the cell or in a culture of the cells may be conducted through strain construction, and/or physically during culture as described herein. For example, the cell may be constructed to express functional components of an "upstream" MEP pathway, and one or more components of a "downstream" terpenoid synthesis pathway. The upstream and downstream pathways may be balanced to control indole accumulation, using a variety of genetic tools, including but not limited to selecting a gene copy number for one or more upstream or downstream pathway enzymes; increasing or decreasing the expression level of the upstream and downstream pathway genes (as individual genes or as operons) using promoters with different or similar strengths and/or modifications to ribosomal binding sites; replacing native genes in the downstream or upstream pathway with heterologous genes coding for homologous enzymes; codon-optimization of one or more heterologous enzymes in the upstream or downstream pathway; amino acid mutations in one or more genes of the downstream and/or upstream pathway; and modifying the order of upstream and downstream pathway genes in a heterologous operon.

In some embodiments, the cell comprises at least one additional copy of at least one of dxs, idi, ispD, and ispF, which in some embodiments is a heterologous dxs-idi-ispDF operon.

The accumulation of indole can be a proxy for the efficiency of terpenoid production, and thus the genetic elements may provide for accumulation of indole in the culture at less than 100 mg/L, or in other embodiments at less than 50 mg/L, at less than 10 mg/L, or at less than 1 mg/L.

In these or other embodiments, accumulation of indole in the cell or in a culture of the cells is controlled by modifying or regulating the indole pathway, or by removing the accumulated indole from the cell culture through chemical methods, including the use of one or more absorbents or scavengers. In various embodiments, the amount of indole in the culture is continuously or intermittently monitored.

In various embodiments, the terpenoid is one or more of steviobioside, stevioside, rebaudioside A, rebaudioside B, rebaudioside C, rebaudioside D, rebaudioside E, rebaudioside F, and dulcoside A, which may be produced in accordance with pathways described herein. Generally, the pathway is constructed at least in-part in a microbial system, employing an upstream MEP pathway, and at least one, two, or three or more components of a downstream terpenoid synthesis pathway. For example, the cell may express a copalyl diphosphate synthase (CPS) enzyme, a kaurene synthase (KS) enzyme, and a GGPPS enzyme. In some embodiments, the cell may further express a kaurene oxidase (KO) enzyme, kaurenoic acid 13-hydroxylase (KAH) enzyme and/or catalytically active portion of KO and KAH fused to a cytochrome P450 reductase enzyme. In still other embodiments, the cell expresses one or more UDP-glycosyltransferases (UGTs) or a catalytically active portion(s) thereof. Exemplary UGTs include UDP-glycosyltransferase (UGT) enzyme(s) from *Stevia* (e.g. *Stevia rebaudiana* Bertoni), or catalytically active portion(s), optionally expressed together on an operon. The UGTs may be expressed from a plasmid or integrated into the host genome.

Optionally, glycosyltransferase steps may take place ex vivo after recovery of the terpenoid substrate from cells.

The terpenoid produced by the method is incorporated into a product, such as a food product or beverage, where the terpenoid is a taste enhancer or bitter blocker. Exemplary products include dessert, yogurt, confectionery, sauce, pickle, delicacy, sweet corn, bread, biscuit, or soft drink. Other products include carbonated or non-carbonated drinks (including low-calorie beverages), cordials, milk, soy, mineral drink, canned fruit, jam, juice, ice cream, dietary product (e.g., low calorie products packaged for weight loss or weight control), cake, biscuit, pastry, dessert, sugar free beer, alcoholic beverage, topping, sauce, chutney, spread, cereal, muesli bar, and confectioneries.

EXAMPLES

Methods

Strains, Plasmids, Oligonucleotides and Genes

*E. coli* K12MG1655 Δ(recA,endA) and *E. coli* K12MG1655Δ(recA,endA)ED3 strains were used as the host strain of karuene strain construction. The sequences of geranylgeranyl pyrophosphate synthase (GGPPS), Copalyl pyrophosphate synthase (C), and Karuene Synthase (K) were obtained from *Taxus canadensis* and *Stevia rebaudiana* (Genbank accession codes: AF081514, AAB87091 and AF097311). Genes were custom-synthesized (from a commercial vendor) to incorporate *E. coli* translation codon and removal of restriction sites for cloning purposes.

Construction of MEP Pathway (dxs-idi-idpDF Operon) (15)

dxs-idi-ispDF operon was initially constructed by cloning each of the genes from the genome of *E. coli* K12 MG1655 using the primers dxs(s), dxs(a), idi(s), idi(a), ispDF(s) and ispDFI(a) under pET21C+ plasmid with T7 promoter (p20T7MEP). Using the primers dxsidiispDFNcoI (s) and dxsidiispDFKpnI(a) dxs-idi-ispDF operon was sub-cloned into pTrcHis2B (Invitrogen) plasmid after digestion with NcoI and KpnI for pTrcMEP plasmid (p20TrcMEP). p20TrcMEP plasmid digested with MluI and PmeI and cloned into MluI and PmeI digested pACYC184-melA(P2A) plasmid to construct p10TrcMEP plasmid. pTrcMEP plasmid digested with BstZ17I and ScaI and cloned into PvuII digested pCL1920 plasmid to construct p5TrcMEP plasmid.

Construction of Kaurene Pathway (KCG).

The downstream kaurene pathway (KCG) was constructed by cloning PCR fragments of KS, CPS and GGPPS into the NcoI-XhoI, XhoI-EcoRI and EcoRI-SalI sites of pTrcHIS2B plasmid to create p20TrcKCG using the primers KSNcoI(s), KSXhoI(a), CPSXhoI(s), CPSEcoRI(a), GGPPSEcoRI(s)

and GGPPSSalI(a). p5T7KCG was constructed by subcloning the NcoI/SalI digested KCG operon from p20TrcKCG into NcoI/SalI digested pCL1920T7 plasmid.

Construction of Chromosomal Integration MEP Pathway Plasmids (15)

For constructing the plasmids with FRP-Km-FRP cassette for amplifying the sequence for integration, p20T7MEP was digested with XhoI/ScaI. FRP-Km-FRP cassette was amplified from the Km cassette with FRP sequence from pkD13 plasmid using the primers KmFRPXhoI(s) and KmFRPScaI (a). The amplified DNA was digested with XhoI/ScaI and cloned into the XhoI/ScaI digested p20T7MEP plasmid (p20T7MEPKmFRP). Similarly the p20TrcMEP plasmid was digested with SacI/ScaI and the amplified DNA using the primers KmFRPSacI(s) and KmFRPScaI(a) was digested, cloned into the p20TrcMEP plasmid (p20TrcMEPKm-FRP).

Chromosomal Integration of the MEP Pathway Cassette (LacIq-MEP-FRP-Km-FRP) Cassette The MEP pathways constructed under the promoters T7 and Trc were localized to the ara operon region in the chromosome with the Kan marker. The PCR fragments were amplified from p20T7MEPKmFRP and p20TrcMEPKm-ERP using the primers IntT7T5(s), IntTrc(s) and Int(a) and then electroporated into E. coli MG1655 recA-end- and E. coli MG1655 recA-end-EDE3 cells for chromosomal integration through the λ Red recombination technique. The site specific localization was confirmed and the Km marker was removed through the action of the FLP recombinase after successful gene integration.

Culture Growth for Screening the Kaurene Production

Single transformants of pre-engineered E. coli strains harboring the appropriate plasmid with upstream (MEP), downstream kaurene pathway were cultivated for 18 h at 30° C. in Luria-Bertani (LB) medium (supplemented with appropriate antibiotics, 100 mg/mL carbenecilin, 34 mg/mL chloramphenicol, 25 mg/L kanamycin or 50 mg/L spectinomycin). For small scale cultures to screen the engineered strains, these preinnoculum were used to seed fresh 2-mL defined feed medium containing 0.5% yeast extract and 20% (v/v) dodecane (13.3 g/L $KH_2PO_4$, 4 g/L $(NH_4)_2HPO_4$, 1.7 g/L citric acid, 0.0084 g/L EDTA, 0.0025 g/L $CoCl_2$, 0.015 g/L $MnCl_2$, 0.0015 g/L $CuCl_2$, 0.003 g/L $H_3BO_3$, 0.0025 g/L $Na_2MoO_4$, 0.008 g/L $Zn(CH_3COO)_2$, 0.06 g/L Fe(III) citrate, 0.0045 g/L thiamine, 1.3 g/L $MgSO_4$, 10 g/L glycerol, 5 g/L yeast extract, pH 7.0). The culture was maintained with appropriate antibiotics and 100 mM IPTG for gene induction at 22° C. for 5 days.

GC-MS Analysis of Kaurene

For analysis of kaurene accumulation from small scale culture, 1.5 mL of the culture was vortexed with 1 mL hexane for 30 min. The mixture was centrifuged to separate the organic layer. For bioreactor 1 uL of the dodecane layer was diluted to 200 uL using hexane. 1uL of the hexane layer was analyzed by GC-MS (Varian saturn 3800 GC attached to a Varian 2000 MS). The sample was injected into a HP5 ms column (30 m×250 uM×0.25 uM thickness) (Agilent Technologies USA). Helium (ultra purity) at a flow rate 1.0 ml/min was used as a carrier gas. The oven temperature was first kept constant at 50° C. for 1 min, and then increased to 220° C. at to the increment of 10° C./min, and finally held at this temperature for 10 min. The injector and transfer line temperatures were set at 200° C. and 250° C., respectively. Pure taxadiene was used as a standard for the quantitative measurement of kaurene production from engineered strains.

Example 1

Engineering Karuene Biosynthesis in E. coli

Figure 3:
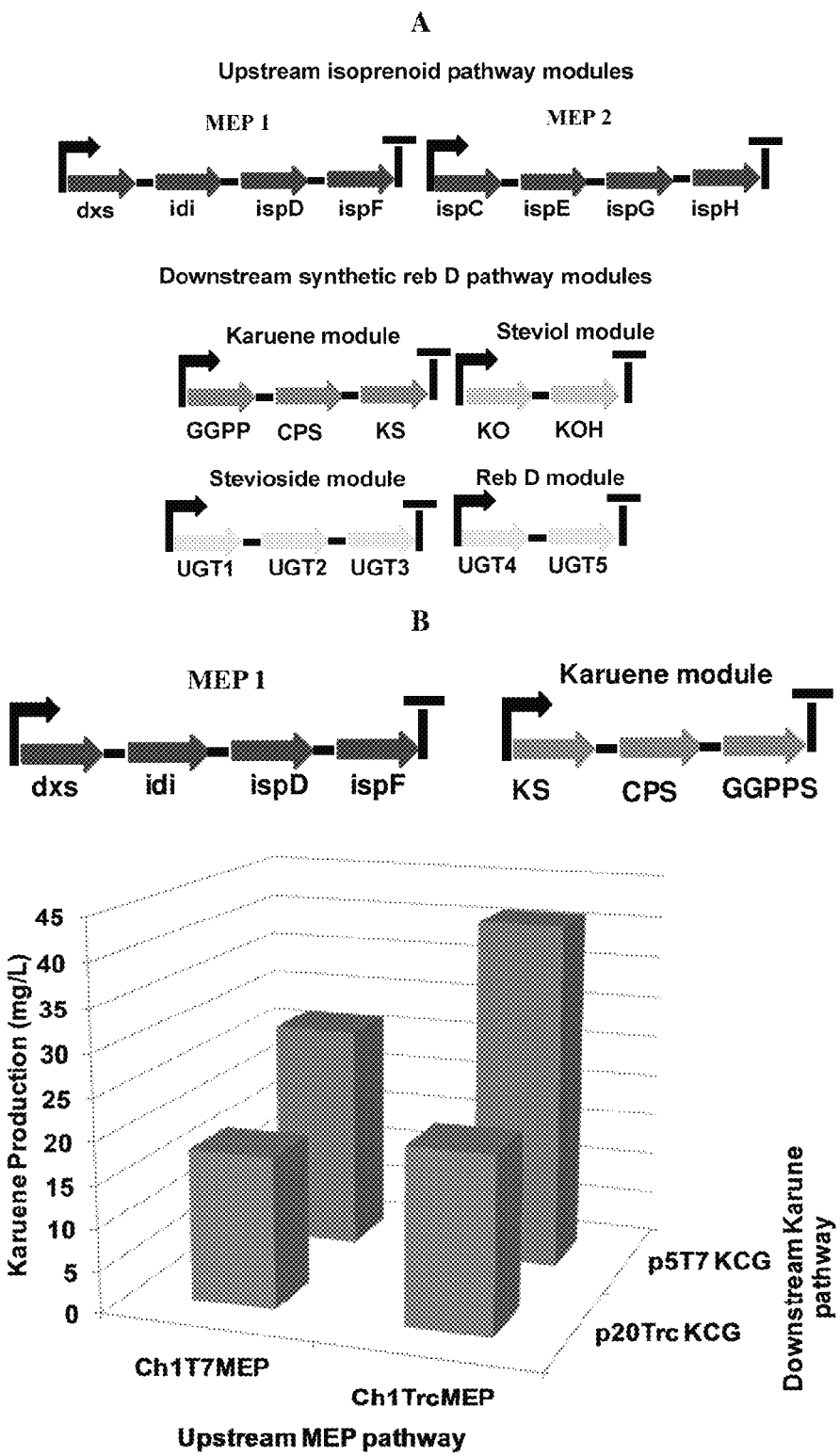
FIG. 3. Multivariate-modular engineering of steviol glycosides. (A) Modularization of rebaudioside D (Reb D) biosynthetic pathway. (B) Schematics of the modular pathway and the production of committed cyclic diterpenoid precursor kaurene from the engineered *E. coli* strains. Experimentation with four strains on a small upstream and downstream expression profile showed significant differences in kaurene production between strains, with one *E. coli* strain showing production of 45 mg/L.

The upstream MEP pathway module, dxs-idi-ispdF, was cloned under the control of two synthetic promoters with low (Trc) and high (T7) strength. The MEP pathway is further localized into the chromosome of the E. coli MG1655 recA-EndA-strain for the overproduction of the upstream isoprenoid metabolites and downstream kaurene. The putative downstream pathway for the biosynthesis of kaurene, GPPP synthase (G), Copalyl pyrophosphate synthase (C), and Karuene Synthase (K), was cloned under two promoters (Trc and T7) using a 20 copy (p20Trc-KCG) and 5 copy plasmid (p5T7-KCG). The downstream pathways was transferred into the upstream chromosomal MEP pathway engineered strains. A total of 4 strains were constructed with varying upstream and downstream pathway to understand the variation in kaurene production corresponding to the pathway strengths. FIG. 3B summarizes the details of strain construction and results of kaurene accumulation from engineered E. coli strains. Clearly, the balancing of the upstream and downstream pathway is key for the high accumulation of kaurene. This is the first example of microbial production of the steviol glycoside precursor scaffold kaurene.

Example 2

Metabolite Indole Accumulation Inversely Correlates with Karuene

Figure 4:
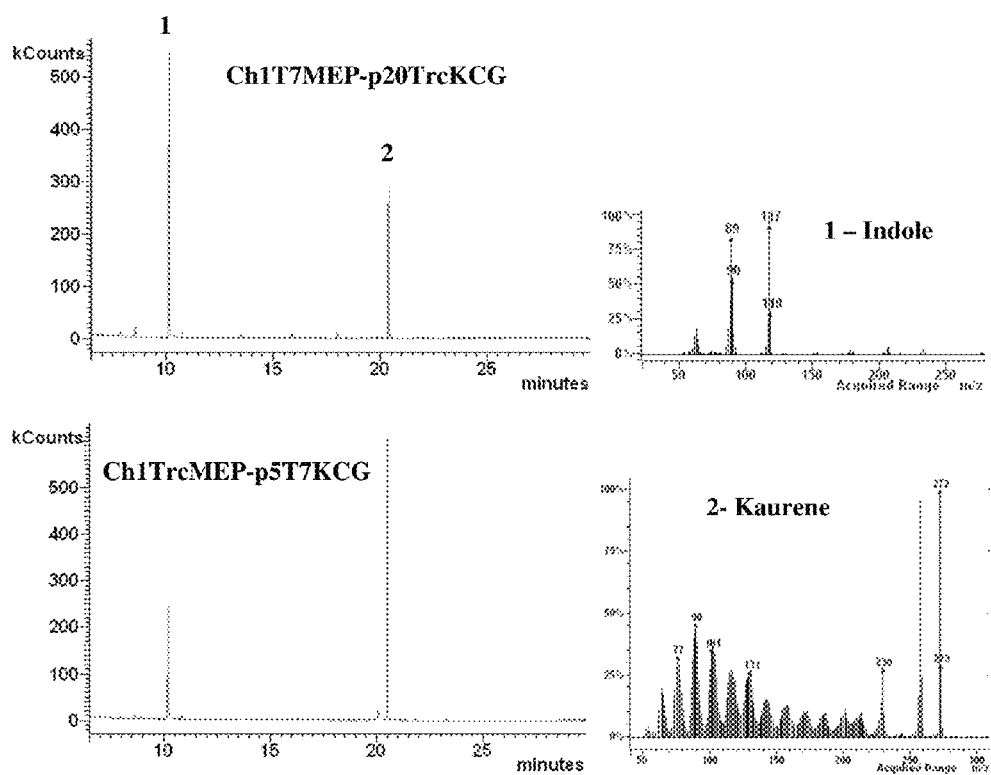
FIG. 4. Correlation between indole accumulation and kaurene production. The to GC chromatograph of the two strains show low (Ch1T7MEP-p20TrcKCG) and high (Ch1TreMEP-p5T7KCG) accumulation of kaurene. The peak 1 and 2 corresponds to indole and kaurene respectively. The corresponding MS spectra are shown in the right.

Metabolomic analysis of the engineered strains identified the accumulation of the metabolite indole that correlated strongly with pathway expression levels and kaurene production (FIG. 4). The corresponding peaks in the gas chromatography-mass spectrometry (GC-MS) chromatogram was identified as indole and kaurene.

TABLE 2

Details of plasmids constructed for the study

| No | Plasmid | Origin of replication | Antibiotic marker |
|---|---|---|---|
| 1 | p20T7MEP | pBR322 | Amp |
| 2 | p20TrcMEP | pBR322 | Amp |
| 4 | p20T7MEPKmFRP | pBR322 | Km |
| 6 | p20TrcMEPKm-FRP | pBR322 | Km |
| 9 | p20TrcKCG | pBR322 | Amp |
| 13 | p5T7KCG | SC101 | Spect |

TABLE 3

Details of the primers used for the cloning of plasmids, and chromosomal delivery of the MEP pathway.

| Primer Name | Sequences |
|---|---|
| dxsNdeI(s) | CGGCATATGAGTTTTGATATTGCCAAATACCCG (SEQ ID NO: 17) |

TABLE 3-continued

Details of the primers used for the cloning of plasmids, and chromosomal delivery of the MEP pathway.

| Primer Name | Sequences |
| --- | --- |
| dxsNheI(a) | CGGCTAGCTTATGCCAGCCAGGCCTTGATTTTG<br>(SEQ ID NO: 18) |
| idiNheI(s) | CGCGGCTAGCGAAGGAGATATACATATGCAAACGGAACACG<br>TCATTTTATTG<br>(SEQ ID NO: 19) |
| idiEcoRI(a) | CGGAATTCGCTCACAACCCCGGCAAATGTCGG<br>(SEQ ID NO: 20) |
| ispDFEcoRI(s) | GCGAATTCGAAGGAGATATACATATGGCAACCACTCATTTG<br>GATGTTTG<br>(SEQ ID NO: 21) |
| ispDFXhoI(a) | GCGCTCGAGTCATTTTGTTGCCTTAATGAGTAGCGCC<br>(SEQ ID NO: 22) |
| dxsidiispDFNcoI(s) | TAAACCATGGGTTTTGATATTGCCAAATACCCG<br>(SEQ ID NO: 23) |
| dxsidiispDFKpnI(a) | CGGGGTACCTCATTTTGTTGCCTTAATGAGTAGCGC<br>(SEQ ID NO: 24) |
| dxsidiispDFXhoI(a) | CGGCTCGAGTCATTTTGTTGCCTTAATGAGTAGCGC<br>(SEQ ID NO: 25) |
| T5AgeI(s) | CGTAACCGGTGCCTCTGCTAACCATGTTCATGCCTTC<br>(SEQ ID NO: 26) |
| T5NheI(a) | CTCCTTCGCTAGCTTATGCCAGCC<br>(SEQ ID NO: 27) |
| GGPPSEcoRI(s) | CGTAGAATTCAGAAGGAGATATACATATGTTTGATTTCAATG<br>AATATATGAAAAGTAAGGC<br>(SEQ ID NO: 28) |
| GGPPSSalI(a) | GATGGTCGACTCACAACTGACGAAACGCAATGTAATC<br>(SEQ ID NO: 29) |
| KSNcoI(s) | ACCATGGCTCTGTCTCTGTGCATT<br>(SEQ ID NO: 30) |
| KSXhoI(a) | TCTCGAGTTAACGTTGTTCTTCGTTTTCG<br>(SEQ ID NO: 31) |
| CPSXhoI(s) | ACTCGAGAAGAAGGAGATATACATATGAAGACTGG<br>(SEQ ID NO: 32) |
| CPSEcoRI(a) | TGAATTCTCAGATTACGATTTCAAATACTTTGG<br>(SEQ ID NO: 33) |
| KmFRPXhoI(s) | GACGCTCGAGGAGCAATAACTAGCATAACCCCTTGGGGCCT<br>CTAAACGGGTCTTGAGGGGTTTTTTGCTTGTGTAGGCTGGAG<br>CTGCTTCG<br>(SEQ ID NO: 34) |
| KmFRPScaI(a) | GACGAGTACTGAACGTCGGAATTGATCCGTCGAC<br>(SEQ ID NO: 35) |
| KmFRPSacI(s) | GACGGAGCTCGAGCAATAACTAGCATAACCCCTTGGGGCCT<br>CTAAACGGGTCTTGAGGGGTTTTTTGCTTGTGTAGGCTGGAG<br>CTGCTTCG<br>(SEQ ID NO: 36) |
| IntT7T5(s) | ATGACGATTTTTGATAATTATGAAGTGTGGTTTGTCATTGCA<br>TTAATTGCGTTGCGCTCACTG<br>(SEQ ID NO: 37) |
| IntTrc(s) | ATGACGATTTTTGATAATTATGAAGTGTGGTTTGTCATTGGC<br>ATCCGCTTACAGACAAGCTGTG<br>(SEQ ID NO: 38) |

TABLE 3-continued

Details of the primers used for the cloning of
plasmids, and chromosomal delivery of the MEP pathway.

| Primer Name | Sequences |
|---|---|
| Int(a) | TTAGCGACGAAACCCGTAATACACTTCGTTCCAGCGCAGCC<br>GACGTCGGAATTGATCCGTCGAC<br>(SEQ ID NO: 39) |

Table 4. Exemplary protein sequences. Enzyme sequences in accordance with aspects of the invention may be as defined below. Alternatively, the enzymes may be optimized through processes and parameters as described herein, and generally producing amino acid sequences that are at least 60%, at least 70%, at least 80%, at least 90%, at least 95%, or at least 98% identical to the amino acid sequences shown below, including with respect to the full length sequence or a catalytically active truncated sequence.

```
GGPP synthase (T. canadensis: AF081514)-
                                                      SEQ ID NO: 1
MFDFNEYMKSKAVAVDAALDKAIPLEYPEKIHESMRYSLLAGGKRVRPALCIAACE

LVGGSQDLAMPTACAMEMIHTMSLIHDDLPCMDNDDFRRGKPTNHKVFGEDTAVL

AGDALLSFAFEHIAVATSKTVPSDRTLRVISELGKTIGSQGLVGGQVVDITSEGDANV

DLKTLEWIHIHKTAVLLECSVVSGGILGGATEDEIARIRRYARCVGLLFQVVDDILDV

TKSSEELGKTAGKDLLTDKATYPKLMGLEKAKEFAAELATRAKEELSSFDQIKAAPL

LGLADYIAFRQN

GGPP synthase (Stevia rebaudiana: ABD92926)-
                                                      SEQ ID NO: 2
MALVNPTALFYGTSIRTRPTNLLNPTQKLRPVSSSSLPSFSSVSAILTEKHQSNPSENN

NLQTHLETPFNFDSYMLEKVNMVNEALDASVPLKDPIKIHESMRYSLLAGGKRIRPM

MCIAACEIVGGNILNAMPAACAVEMIHTMSLVHDDLPCMDNDDFRRGKPISHKVYG

EEMAVLTGDALLSLSFEHIATATKGVSKDRIVRAIGELARSVGSEGLVAGQVVDILSE

GADVGLDHLEYIHIHKTAMLLESSVVIGAIMGGGSDQQIEKLRKFARSIGLLFQVVDD

ILDVTKSTEELGKTAGKDLLTDKTTYPKLLGIEKSREFAEKLNKEAQEQLSGFDRRK

AAPLIALANYNAYRQN

Copalyl pyrophosphate synthase (Stevia rebaudiana: AAB87091)-
                                                      SEQ ID NO: 3
MKTGFISPATVFHHRISPATTFRHHLSPATTNSTGIVALRDINFRCKAVSKEYSDLLQK

DEASFTKWDDDKVKDHLDTNKNLYPNDEIKEFVESVKAMFGSMNDGEINVSAYDT

AWVALVQDVDGSGSPQFPSSLEWIANNQLSDGSWGDHLLFSAHDRIINTLACVIALT

SWNVHPSKCEKGLNFLRENICKLEDENAEHMPIGFEVTFPSLIDIAKKLNIEVPEDTPA

LKEIYARRDIKLTKIPMEVLHKVPTTLLHSLEGMPDLEWEKLLKLQCKDGSFLFSPSS

TAFALMQTKDEKCLQYLTNIVTKFNGGVPNVYPVDLFEHIWVVDRLQRLGIARYFK

SEIKDCVEYINKYWTKNGICWARNTHVQDIDDTAMGFRVLRAHGYDVTPDVFRQFE

KDGKFVCFAGQSTQAVTGMFNVYRASQMLFPGERILEDAKKFSYNYLKEKQSTNEL

LDKWIIAKDLPGEVGYALDIPWYASLPRLETRYYLEQYGGEDDVWIGKTLYRMGYV

SNNTYLEMAKLDYNNYVAVLQLEWYTIQQWYVDIGIEKFESDNIKSVLVSYYLAAA

SIFEPERSKERIAWAKTTILVDKITSIFDSSQSSKEDITAFIDKFRNKSSSKKHSINGEPW

HEVMVALKKTLHGFALDALMTHSQDIHPQLHQAWEMWLTKLQDGVDVTAELMVQ
```

```
MINMTAGRWVSKELLTHPQYQRLSTVTNSVCHDITKLHNFKENSTTVDSKVQELVQ

LVFSDTPDDLDQDMKQTFLTVMKTFYYKAWCDPNTINDHISKVFEIVI
```

Kaurene synthase (*Stevia rebaudiana*: AF097311_1)-
SEQ ID NO: 4

```
MNLSLCIASPLLTKSNRPAALSAIHTASTSHGGQTNPTNLIIDTTKERIQKQFKNVEISV

SSYDTAWVAMVPSPNSPKSPCFPECLNWLINNQLNDGSWGLVNHTHNHNHPLLKDS

LSSTLACIVALKRWNVGEDQINKGLSFIESNLASATEKSQPSPIGFDIIFPGLLEYAKNL

DINLLSKQTDFSLMLHKRELEQKRCHSNEMDGYLAYISEGLGNLYDWNMVKKYQM

KNGSVFNSPSATAAAFINHQNPGCLNYLNSLLDKFGNAVPTVYPHDLFIRLSMVDTIE

RLGISHHFRVEIKNVLDETYRCWVERDEQIFMDVVTCALAFRLLRINGYEVSPDPLAE

ITNELALKDEYAALETYHASHILYQEDLSSGKQILKSADFLKEIISTDSNRLSKLIHKE

VENALKFPINTGLERINTRRNIQLYNVDNTRILKTTYHSSNISNTDYLRLAVEDFYTCQ

SIYREELKGLERWVVENKLDQLKFARQKTAYCYFSVAATLSSPELSDARISWAKNGI

LTTVVDDFFDIGGTIDELTNLIQCVEKWNVDVDKDCCSEHVRILFLALKDAICWIGDE

AFKWQARDVTSHVIQTWLELMNSMLREAIWTRDAYVPTLNEYMENAYVSFALGPI

VKPAIYFVGPKLSEEIVESSEYHNLFKLMSTQGRLLNDIHSFKREFKEGKLNAVAHL

SNGESGKVEEEVVEEMMMMIKNKRKELMKLIFEENGSIVPRACKDAFWNMCHVLN

FFYANDDGFTGNTILDTVKDIIYNPLVLVNENEEQR
```

Kaurene oxidase (*Stevia rebaudiana*: ABA42921)-
SEQ ID NO: 5

```
MDAVTGLLTVPATAITIGGTAVALAVALIFWYLKSYTSARRSQSNHLPRVPEVPGVP

LLGNLLQLKEKKPYMTFTRWAATYGPIYSIKTGATSMVVVSSNEIAKEALVTRFQSIS

TRNLSKALKVLTADKTMVAMSDYDDYHKTVKRHILTAVLGPNAQKKHRIHRDIMM

DNISTQLHEFVKNNPEQEEVDLRKIFQSELFGLAMRQALGKDVESLYVEDLKITMNR

DEIFQVLVVDPMMGAIDVDWRDFFPYLKWVPNKKFENTIQQMYIRREAVMKSLIKE

HKKRIASGEKLNSYIDYLLSEAQTLTDQQLLMSLWEPIIESSDTTMVTTEWAMYELA

KNPKLQDRLYRDIKSVCGSEKITEEHLSQLPYITAIFHETLRRHSPVPIIPLRHVHEDTV

LGGYHVPAGTELAVNIYGCNMDKNVWENPEEWNPERFMKENETIDFQKTMAFGGG

KRVCAGSLQALLTASIGIGRMVQEFEWKLKDMTQEEVNTIGLTTQMLRPLRAIIKPRI
```

Ent-kaurenoic acid 13-hydroxylase (*Stevia rebaudiana*: ACD93722)-
SEQ ID NO: 6

```
MIQVLTPILLFLIFFVFWKVYKHQKTKINLPPGSFGWPFLGETLALLRAGWDSEPERF

VRERIKKHGSPLVFKTSLFGDRFAVLCGPAGNKFLFCNENKLVASWWPVPVRKLFG

KSLLTIRGDEAKWMRKMLLSYLGPDAFATHYAVTMDVVTRRHIDVHWRGKEEVN

VFQTVKLYAFELACRLFMNLDDPNHIAKLGSLFNIFLKGIIELPIDVPGTRFYSSKKAA

AAIRIELKKLIKARKLELKEGKASSSQDLLSHLLTSPDENGMFLTEEEIVDNILLLLFA

GHDTSALSITLLMKTLGEHSDVYDKVLKEQLEISKTKEAWESLKWEDIQKMKYSWS

VICEVMRLNPPVIGTYREALVDIDYAGYTIPKGWKLHWSAVSTQRDEANFEDVTRFD

PSRFEGAGPTPFTFVPFGGGPRMCLGKEFARLEVLAFLHNIVTNFKWDLLIPDEKIEY

DPMATPAKGLPIRLHPHQV
```

```
Taxus NADPH: cytochrome P450 reductase (Taxus cuspidate:
AY571340)-
                                                    SEQ ID NO: 7
MQANSNTVEGASQGKSLLDISRLDHIFALLLNGKGGDLGAMTGSALILTENSQNLMI

LTTALAVLVACVFFFVWRRGGSDTQKPAVRPTPLVKEEDEEEEDDSAKKKVTIFFGT

QTGTAEGFAKALAEEAKARYEKAVFKVVDLDNYAADDEQYEEKLKKEKLAFFMLA

TYGDGEPTDNAARFYKWFLEGKEREPWLSDLTYGVFGLGNRQYEHFNKVAKAVDE

VLIEQGAKRLVPVGLGDDDQCIEDDFTAWREQVWPELDQLLRDEDDEPTSATPYTA

AIPEYRVEIYDSVVSVYEETHALKQNGQAVYDIHHPCRSNVAVRRELHTPLSDRSCIH

LEFDISDTGLIYETGDHVGVHTENSIETVEEAAKLLGYQLDTIFSVHGDKEDGTPLGG

SSLPPPFPGPCTLRTALARYADLLNPPRKAAFLALAAHASDPAEAERLKFLSSPAGKD

EYSQWVTASQRSLLEIMAEFPSAKPPLGVFFAAIAPRLQPRYYSISSSPRFAPSRIHVTC

ALVYGPSPTGRIHKGVCSNWMKNSLPSEETHDCSWAPVFVRQSNFKLPADSTTPIVM

VGPGTGFAPFRGFLQERAKLQEAGEKLGPAVLFFGCRNRQMDYIYEDELKGYVEKG

ILTNLIVAFSREGATKEYVQHKMLEKASDTWSLIAQGGYLYVCGDAKGMARDVHR

TLHTIVQEQESVDSSKAEFLVKKLQMDGRYLRDIW

Stevia NADPH: cytochrome P450 reductase
(Stevia rebaudiana: ABB88839)-
                                                    SEQ ID NO: 8
MQSDSVKVSPFDLVSAAMNGKAMEKLNASESEDPTTLPALKMLVENRELLTLFTTS

FAVLIGCLVFLMWRRSSSKKLVQDPVPQVIVVKKKEKESEVDDGKKKVSIFYGTQTG

TAEGFAKALVEEAKVRYEKTSFKVIDLDDYAADDDEYEEKLKKESLAFFFLATYGD

GEPTDNAANFYKWFTEGDDKGEWLKKLQYGVFGLGNRQYEHFNKIAIVVDDKLTE

MGAKRLVPVGLGDDDQCIEDDFTAWKELVWPELDQLLRDEDDTSVTTPYTAAVLE

YRVVYHDKPADSYAEDQTHTNGHVVHDAQHPSRSNVAFKKELHTSQSDRSCTHLEF

DISHTGLSYETGDHVGVYSENLSEVVDEALKLLGLSPDTYFSVHADKEDGTPIGGAS

LPPPFPPCTLRDALTRYADVLSSPKKVALLALAAHASDPSEADRLKFLASPAGKDEY

AQWIVANQRSLLEVMQSFPSAKPPLGVFFAAVAPRLQPRYYSISSSPKMSPNRIHVTC

ALVYETTPAGRIHRGLCSTWMKNAVPLTESPDCSQASIFVRTSNFRLPVDPKVPVIMI

GPGTGLAPFRGFLQERLALKESGTELGSSIFFFGCRNRKVDFIYEDELNNFVETGALSE

LIVAFSREGTAKEYVQHKMSQKASDIWKLLSEGAYLYVCGDAKGMAKDVHRTLHT

IVQEQGSLDSSKAELYVKNLQMSGRYLRDVW

UDP-glucosyltransferase-1 (Stevia rebaudiana: AAM53963)-
                                                    SEQ ID NO: 9
MATSDSIVDDRKQLHVATFPWLAFGHILPFLQLSKLIAEKGHKVSFLSTTRNIQRLSS

HISPLINVVQLTLPRVQELPEDAEATTDVHPEDIQYLKKAVDGLQPEVTRFLEQHSPD

WIIYDFTHYWLPSIAASLGISRAYFCVITPWTIAYLAPSSDAMINDSDGRTTVEDLTTP

PKWFPFPTKVCWRKHDLARMEPYEAPGISDGYRMGMVFKGSDCLLFKCYHEFGTQ

WLPLLETLHQVPVVPVGLLPPEIPGDEKDETWVSIKKWLDGKQKGSVVYVALGSEA

LVSQTEVVELALGLELSGLPFVWAYRKPKGPAKSDSVELPDGFVERTRDRGLVWTS

WAPQLRILSHESVCGFLTHCGSGSIVEGLMFGHPLIMLPLFGDQPLNARLLEDKQVGI

EIPRNEEDGCLTKESVARSLRSVVVENEGEIYKANARELSKIYNDTKVEKEYVSQFV

DYLEKNARAVAIDHES
```

-continued

UDP-glucosyltransferase-2 (*Stevia rebaudiana*: AAR06921)-
SEQ ID NO: 10
MPISDINAGSHILVFPYPAQGHMLTLLDLTHQLAIRNLTITILVTPKNLPTISPLLAAHP
TTVSALLLPLPPHPAIPSGIENVKDLPNDAFKAMMVALGDLYNPLRDWFRNQPNPPV
AIISDFFLGWTHHLAVELGIRRYTFSPSGALALSVIFSLWRYQPKRIDVENEKEAIKFP
KIPNSPEYPWWQLSPIYRSYVEGDPDSEFIKDGFLADIASWGIVINSFTELEQVYVDHL
KHELGHDQVFAVGPLLPPGDKTSGRGGSSSNDVLSWLDTCADRTVVYVCFGSQMV
LTNGQMEVVALGLEKSRVKFVWSVKEPTVGHEAANYGRVPPGFEDRVSGRGLVIR
GWVPQVAILSHDSVGVFLTHCGWNSVMEAVAAEVLMLTWPMSADQFSNATLLHEL
KVGIKVCEGSNIVPNSDELAELFSKSLSDETRLERKRVKEFAKSAKEAVGPKGSSVGE
LERLVDNLSL UDP-glucosyltransferase-3 (*Stevia rebaudiana*: AAR06920)-
SEQ ID NO: 11
MAEQQKIKKSPHVLLIPFPLQGHINPFIQFGKRLISKGVKTTLVTTIHTLNSTLNHSNTT
TTSIEIQAISDGCDEGGFMSAGESYLETFKQVGSKSLADLIKKLQSEGTTIDAIIYDSMT
EWVLDVAIEFGIDGGSFFTQACVVNSLYYHVHKGLISLPLGETVSVPGFPVLQRWET
PLILQNHEQIQSPWSQMLFGQFANIDQARWVFTNSFYKLEEEVIEWTRKIWNLKVIGP
TLPSMYLDKRLDDDKDNGFNLYKANHHECMNWLDDKPKESVVYVAFGSLVKHGP
EQVEEITRALIDSDVNFLWVIKHKEEGKLPENLSEVIKTGKGLIVAWCKQLDVLAHES
VGCFVTHCGFNSTLEAISLGVPVVAMPQFSDQTTNAKLLDEILGVGVRVKADENGIV
RRGNLASCIKMIMEEERGVIIRKNAVKWKDLAKVAVHEGGSSDNDIVEFVSELIKA UDP-glucosyltransferase-4 (*Stevia rebaudiana*: AAR06917)-
SEQ ID NO: 12
MSPKMVAPPTNLHFVLFPLMAQGHLVPMVDIARILAQRGATVTIITTPYHANRVRPV
ISRAIATNLKIQLLELQLRSTEAGLPEGCESFDQLPSPEYWKNISTAIDLLQQPAEDLLR
ELSPPPDCIISDFLFPWTTDVARRLNIPRLVFNGPGCFYLLCIHVAITSNILGENEPVSSN
TERVVLPGLPDRIEVTKLQIVGSSRPANVDEMGSWLRAVEAEKASFGIVVNTFEELEP
EYVEEYKTVKDKKMWCIGPVSLCNKTGPDLAERGNKAAITEHNCLKWLDERKLGS
VLYVCLGSLARISAAQAIELGLGLESINRPFIWCVRNETDELKTWFLDGFEERVRDRG
LIVHGWAPQVLILSHPTIGGFLTHCGWNSTIESITAGVPMITWPFFADQFLNEAFIVEV
LKIGVRIGVERACLFGEEDKVGVLVKKEDVKKAVECLMDEDEDGDQRRKRVIELAK
MAKIAMAEGGS SYENVSSLIRDVTETVRAPH UDP-glucosyltransferase-5 (*Stevia rebaudiana*: AAN40684)-
SEQ ID NO: 13
MSLKGNDKELHLVMFPFFAFGHITPFVQLSNKISSLYPGVKITFLAASASVSRIETMLN
PSTNTKVIPLTLPRVDGLPEGVENTADASPATIGLLVVAIDLMQPQIKTLLANLKPDF
VIFDFVHWWLPEIASELGIKTIYFSVYMANIVMPSTSKLTGNKPSTVEDIKALQQSDGI
PVKTFEAISLMNVFKSFHDWMDKCINGCNLMLIKSCREMEGSRIDDVTKQSTRPVFLI
GPVVPEPHSGELDETWANWLNRFPAKSVIYCSFGSETFLTDDQIRELALGLELTGLPF
FLVLNFPANVDKSAELKRTLPDGFLERVKDKGIVHSGWVQQRHILAHDSVGCYVFH
AGYGSVIEGLVNDCQLVMLPMKVDQFTNSKVIALELKAGVEVNRRDEDGYFGKDD
VFEAVESVMMDTENEPAKSIRENHRKLKEFLQNDEIQKKYIADFVENLKAL UDP-glucosyltransferase-6 (*Stevia rebaudiana*: ACE87855)-
SEQ ID NO: 14

MATSDSIVDDRKQLHVATFPWLAFGHILPYLQLSKLIAEKGHKVSFLSTTRNIQRLSS

HISPLINVVQLTLPRVQELPEDAEATTDVHPEDIPYLKKASDGLQPEVTRFLEQHSPD

WIIYDYTHYWLPSIAASLGISRAHFSVTTPWAIAYMGPSADAMINGSDGRTTVEDLTT

PPKWFPFPTKVCWRKHDLARLVPYKAPGISDGYRMGLVLKGSDCLLSKCYHEFGTQ

WLPLLETLHQVPVVPVGLLPPEVPGDEKDETWVSIKKWLDGKQKGSVVYVALGSEV

LVSQTEVVELALGLELSGLPFVWAYRKPKGPAKSDSVELPDGFVERTRDRGLVWTS

WAPQLRILSHESVCGFLTHCGSGSIVEGLMFGHPLIMLPIFGDQPLNARLLEDKQVGI

EIPRNEEDGCLTKESVARSLRSVVVEKEGEIYKANARELSKIYNDTKVEKEYVSQFV

DYLEKNTRAVAIDHES

REFERENCES

1. M. Sharma, N. K. Thakral, S. Thakral, *Natural Product Radiance* 8, 181 (2009).
2. M. C. Carakostas, L. L. Curry, A. C. Boileau, D. J. Brusick, *Food Chem Toxicol* 46 Suppl 7, Si (July, 2008).
3. S. R. Mishra P., Kumar U. and Prakash V, *Global Journal of Biotechnology & Biochemistry* 5, 62 (2010).
4. S. D. Singh, G. P. Rao, *Sugar Tech* 7, 17 (2005).
5. P. K. Ajikumar et al., *Mol Pharm* 5, 167 (March-April, 2008).
6. M. C. Carakostas, L. L. Curry, A. C. Boileau, D. J. Brusick, *Food and Chemical Toxicology* 46, Si (2008).
7. C. Ulbricht et al., *Cardiovascular & Hematological Agents in Medicinal Chemistry (Formerly Current Medicinal Chemistry-Cardiovascular & Hematological Agents)* 8, 113.
8. J. M. C. Geuns, http://www.eustas.org/Steviol_glycosides_summary_application.pdfSteviol, EUSTAS, (2007).
9. K. E. Tyo, H. S. Alper, G. N. Stephanopoulos, *Trends Biotechnol* 25, 132 (March, 2007).
10. A. S. Richman, M. Gijzen, A. N. Starratt, Z. Yang, J. E. Brandle, *The Plant Journal* 19, 411 (1999).
11. J. Geuns, *Phytochemistry* 64, 913 (2003).
12. A. Richman et al., *The Plant Journal* 41, 56 (2005).
13. D. G. Gibson et al., *Science* 329, 52 (Jul. 2, 2010).
14. V. E. Balderas-Hernandez et al., *Microb Cell Fact* 8, 19 (2009).
15. Ajikumar, P. K., et al., *Science.* 330, 70-4 (October 2010)

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the specific purpose mentioned herein.

---

What is claimed is:

1. A method for producing steviol or steviol glycoside comprising:
  culturing an *E. coli* strain having balanced expression of (1) an upstream methylerythritol pathway (MEP) that produces isopentyl pyrophosphate (IPP) and dimethylallyl pyrophosphate (DMAPP), with respect to (2) a downstream pathway that produces steviol or steviol glycoside from said IPP and DMAPP, the downstream pathway comprising a recombinantly expressed copalyl diphosphate synthase (CPS), kaurene synthase (KS), a geranylgeranyl diphosphate synthase (GGPPS) kaurenoic acid 13-hydroxylase (KAH) and kaurene oxidase (KO), and optionally one or more *Stevia* UDP glycosyl transferase enzymes;
  wherein said balanced expression is obtained by increasing or decreasing the expression level of a downstream pathway module and increasing or decreasing the expression level of an upstream pathway module together in *E. coli*, and identifying an *E. coli* strain with higher production of steviol or steviol glycoside and/or lower accumulation of indole as having balanced expression.

2. The method of claim 1, wherein the copalyl diphosphate synthase (CPS) enzyme is a *Stevia* enzyme.

3. The method of claim 1, wherein the kaurene synthase (KS) enzyme is a *Stevia* enzyme.

4. The method of claim 1, wherein the GGPPS enzyme is a Taxus enzyme or a *Stevia* enzyme.

5. The method of claim 1, wherein the upstream pathway module comprises dxs, idi, ispD, and ispF genes of the MEP pathway.

6. The method of claim 5, wherein the upstream pathway module comprises dxs, idi, ispD and ispF genes of the MEP pathway expressed as the operon dxs-idi-ispD-ispF.

7. The method of claim 1, wherein the downstream module comprises the gene encoding the copalyl diphosphate synthase (CPS) enzyme, the gene encoding the kaurene synthase (KS) enzyme and the gene encoding the GGPPS enzyme co-expressed on an operon.

8. The method of claim 1, wherein the downstream module further comprises kaurene oxidase (KO) and kaurenoic acid 13-hydroxylase (KAH) enzymes co-expressed on an operon, optionally each as fusions with a cytochrome P450 reductase.

9. The method of claim 1, wherein the expression of the upstream pathway module and the expression of the downstream pathway module are balanced by one or more of: increasing or decreasing promoter strengths, increasing or decreasing gene or operon copy number, and changing the position of genes within the module.

10. The method of claim 9, wherein one or more operons is integrated into the *E. coli* genome.

11. The method of claim 1, wherein the KAH and KO are *Stevia* enzymes.

12. The method of claim 11, wherein the KAH and/or KO comprise catalytically active portions fused to a *Stevia* cytochrome P450 reductase enzyme.

13. The method of claim 12, wherein the KAH and KO enzymes have an N-terminal truncation and contain the N-terminal peptide sequence MALLLAVF (SEQ ID NO: 16).

14. The method of claim 1, further comprising recovering the steviol or steviol glycoside.

15. The method of claim 14, wherein the steviol or steviol glycoside is recovered from the gas phase of the culture by adding an organic layer.

* * * * *